US009969771B2

(12) United States Patent
Kim et al.

(10) Patent No.: US 9,969,771 B2
(45) Date of Patent: May 15, 2018

(54) TETRAPEPTIDE HAVING EFFECT OF INHIBITING VEGF-INDUCED ANGIOGENESIS AND USE THEREOF

(71) Applicant: AVIXGEN INC., Seoul (KR)

(72) Inventors: Young Myeong Kim, Chuncheon-si (KR); Yi Yong Baek, Goyang-si (KR); Dong Keon Lee, Chuncheon-si (KR); Jun-Sub Choi, Yongin-si (KR); Min Jung Kim, Seoul-si (KR); Hye Cheong Koo, Gwangmyeong-si (KR)

(73) Assignee: AVIXGEN INC., Seoul (KR)

( * ) Notice: Subject to any disclaimer, the term of this patent is extended or adjusted under 35 U.S.C. 154(b) by 0 days. days.

(21) Appl. No.: 15/222,237

(22) Filed: Jul. 28, 2016

(65) Prior Publication Data

US 2017/0037083 A1 Feb. 9, 2017

(30) Foreign Application Priority Data

Aug. 4, 2015 (KR) .................. 10-2015-0110066

(51) Int. Cl.
*A61K 38/07* (2006.01)
*A61K 38/00* (2006.01)
*C07K 5/10* (2006.01)
*C07K 5/11* (2006.01)

(52) U.S. Cl.
CPC ............ *C07K 5/1019* (2013.01); *A61K 38/00* (2013.01)

(58) Field of Classification Search
CPC .......... A61K 38/07; A61K 38/00; C07K 5/10; C07K 5/1019
USPC .......................... 530/330, 300; 514/21.9, 1.1
See application file for complete search history.

(56) References Cited

U.S. PATENT DOCUMENTS

| | | | | |
|---|---|---|---|---|
| 5,595,756 A | * | 1/1997 | Bally | A61K 9/1272 264/4.1 |
| 6,057,122 A | | 5/2000 | Davidson | |
| 6,200,567 B1 | * | 3/2001 | Lopez | C07K 14/70503 424/130.1 |
| 2003/0198978 A1 | * | 10/2003 | Rozzelle | C12N 9/1252 435/6.11 |
| 2005/0019826 A1 | | 1/2005 | Tournaire et al. | |

FOREIGN PATENT DOCUMENTS

| | | |
|---|---|---|
| KR | 1020050085448 A | 8/2005 |
| KR | 10-0607448 B1 | 8/2006 |
| KR | 1020110046911 A | 5/2011 |
| KR | 1020130076821 A | 7/2013 |
| KR | 1020150010455 A | 1/2015 |
| WO | 97/041824 A2 | 11/1997 |

OTHER PUBLICATIONS

UniProt Q8JFN8, pp. 1-2. Integrated into UniProtKB/TrEMBL Oct. 1, 2002.*
Auerbach et al, "Angiogenesis assays: Problems and pitfalls," Cancer and Metastasis Reviews, 2000, 19: 167-172.*
Jain RK, "Barriers to Drug Delivery in Solid Tumors," Scientific American, 1994, 58-65.*
Sporn et al, "Chemoprevention of cancer," Carcinogenesis, 2000, 21(3): 525-530.*
Gura T, "Systems for Identifying New Drugs Are Often Faulty," Science, 1997, 278(7): 1041-1042.*
Neidle, Stephen, ed., Cancer Drug Design and Discovery, Elsevier/Academy Press, 2008, 427-431.*
Colorectal Cancer from Merck Manual, pp. 1-5. Accessed Aug. 21, 2014.*
Gera Neufeld, et al.,"Vascular endothelial growth factor (VEGF) and its receptors", FASEBJ, 1999, pp. 9-22, vol. 13.
Judah Folkman, "Angiogenesis in cancer, vascular, rheumatoid and other disease", Nature Medicine, 1995, pp. 27-31, vol. 1.
Napoleone Ferrara, et al., "The Biology of VEGF and its receptors", Nature Medicine, 2003, pp. 669-676, vol. 9.
Ralf H. Adams, et al., "Molecular regulation of angiogenesis and lymphangiogenesis", Nat. Rev. Mol. Cell Biol., 2007, pp. 464-478, vol. 8.
Napoleone Ferrara, et al., "Angiogenesis as a therapeutic target", Nature, 2005, pp. 967-974, vol. 438.
Hiroyuki Takahashi, et al., "The vascular endothelial growth factor (VEGF)/VEGF receptor system and its role under physiological and pathological conditions", Clinical Science, 2005, pp. 227-241, vol. 109.
M. Shibuya, et al., "VEGF-VEGFR Signals in Health and Disease", Biomol. Ther., 2014, pp. 1-9, vol. 22.
F. Michael Yakes, et al., "Cabozantinib (XL 184), a Novel MET and VEGFR2 Inhibitor, Simultaneously Suppresses Metastasis, Angiogenesis, and Tumor Growth", Mol. Cancer Therapeutics, 2011, pp. 2298-2308, vol. 10.
Stephen R. Wedges, et al., "ZD6474 Inhibits Vascular Endothelial Growth Factor Signaling, Angiogenesis, and Tumor Growth following Oral Administration", Cancer Res., 2002, pp. 4645-4655, vol. 62.
Weon-Kyoo You, et al., "VEGF and c-Met Blockade Amplify Angiogenesis Inhibition in Pancreatic Islet Cancer", Cancer Res., 2011, pp. 4758-4768, vol. 71.

(Continued)

*Primary Examiner* — Julie Ha
(74) *Attorney, Agent, or Firm* — Sughrue Mion, PLLC

(57) ABSTRACT

Provided are a tetrapeptide for inhibiting VEGF-induced angiogenesis and a use thereof, and particularly, provided is a peptide having the amino acid sequence of R-X1-X2-E (wherein X1 is leucine (L), isoleucine (I) or valine (V), and X2 is tyrosine (Y) or phenylalanine (F)) for inhibiting angiogenesis, or preventing, improving or treating cancer. This research was supported by grants from the National Research Foundation of Korea (NRF) funded by the Ministry of Science, ICT and Future Planning (MSIP), Republic of Korea, in 2011 and 2013 [NRF-2011-0028790 and 2013M3A9B6046563]. The tetrapeptide may effectively inhibit VEGF-induced angiogenesis or growth of cancer cells without a risk of side effects, and therefore may be expected to exhibit an excellent anticancer effect.

6 Claims, 46 Drawing Sheets

(56) References Cited

OTHER PUBLICATIONS

Dana D. Hu-Lowe, et al., "Nonclinical Antiangiogenesis and Antitumor Activities of Axitinib (AG-013736), an Oral, Potent, and Selective Inhibitor of Vascular Endothelial Growth Factor Receptor Tyrosine Kinasas 1, 2, 3", Clin. Cancer, 2008, pp. 7272-7283, vol. 14.

Frank Hilberg, et al., "BIBF 1120: Triple Angiokinase Inhibitor with Sustained Receptor Blockade and Good Antitumor Efficacy", Cancer Res., 2008, pp. 4774-4782, vol. 68.

J.-C. Soria, et al., "Systematic review and meta-analysis of randomised, phase II/III trials adding bevacizumab to platinum-based chemotherapy as first-line treatment in patients with advanced non-small-cell lung cancer", Annals of Oncology, 2013, pp. 20-30, vol. 24.

Seon-Jin Lee, et al., "Fractalkine stimulates angiogenesis by activating the Raf-1/MEK/ERK- and PI3K/Akt/eNOS-dependent signal pathways", Am. J. Physiol. Heart Circ. Physiol., 2006, pp. H2836-H2846, vol. 291.

Ju-Hoon So, et al., "Gicerin/Cd146 is involved in zebrafish cardiovascular development and tumor angiogenesis", Genes Cells, 2010, pp. 1099-1110, vol. 15.

Yihai Cao, et al., "Kringle 5 of Plasminogen is a Novel Inhibitor of Endothelial Cell Growth", Journal of Biological Chemistry, 1997, pp. 22924-22928, vol. 272.

Paul C. Lee, et al., "Impaired wound healing and angiogenesis in eNOS-deficient mice", American Physiological Society, 1999, pp. H1600-H1608, vol. 277.

Kameha R. Kidd, et al., "Fishing for novel angiogenic therapies", British Journal of Pharmacology, 2003, pp. 585-594, vol. 140.

Sumio Isogai, et al., "The Vascular Anatomy of the Developing Zebrafish: An Atlas of Embryonic and Early Larval Development", Developmental Biology, 2001, pp. 278-301, vol. 230.

Ji Greenberg, et al., "VEGF as an inhibitor of tumor vessel maturation: implications for cancer therapy", Expert Opin. Biol. Ther., 2009, pp. 1347-1356, vol. 9.

Ahmed Idbaih, et al., "Therapeutic Application of Noncytotoxic Molecular Targeted Therapy in Gliomas: Growth Factor Receptors and Angiogenesis Inhibitors", Oncologist, 2008, pp. 978-992, vol. 13.

Kristina M. Cook, et al., "Angiogenesis Inhibitors-Current Strategies and Future Prospects", CA Cancer J. Clin., 2010, pp. 222-243, vol. 60.

Henk. M. W. Verheul, et al., "Possible molecular mechanisms involved in the toxicity of angiogenesis inhibition", Nat. Rev. Cancer, 2007, pp. 475-485, vol. 7.

M.S. O'Reilly, et al., "Angiostatin: a novel angiogenesis inhibitor that mediates the suppression of metastases by a Lewis lung carcinoma", Cell, 1994, pp. 315-328, vol. 79.

George S. Sheppard, et al., "Lysyl 4-aminobenzoic acid derivatives as potent small molecule mimetics of plasminogen kringle 5", Bioorganic & Medicinal Chemistry Letters, 2004, pp. 965-966, vol. 14.

Yaning Wang, et al., "Biological activity of bevacizumab, a humanized anti-VEGF antibody in vitro", Angiogenesis, 2004, pp. 335-345, vol. 7.

Yi-Yong Baek, et al., "The tetrapeptide Arg-Leu-Tyr-Glu inhibtis VEGF-induced angiogenesis", Biochemical and Biophysical Research Communications, 2015, pp. 532-537, vol. 463.

\* cited by examiner

| # | Peptide sequence | | | | |
|---|---|---|---|---|---|
| 1 | K | L | Y | D | (SEQ ID NO: 4) |
| 2 | K | L | W | D | (SEQ ID NO: 9) |
| 3 | K | L | F | D | (SEQ ID NO: 7) |
| 4 | K | I | Y | D | (SEQ ID NO: 8) |
| 5 | K | L | Y | E | (SEQ ID NO: 5) |
| 6 | R | L | Y | E | (SEQ ID NO: 2) |
| 7 | R | L | Y | D | (SEQ ID NO: 6) |
| 8 | R | L | M | E | (SEQ ID NO: 10) |
| 9 | R | V | Y | E | (SEQ ID NO: 3) |
| 10 | E | Y | L | R | (SEQ ID NO: 11) |

FIG. 1A

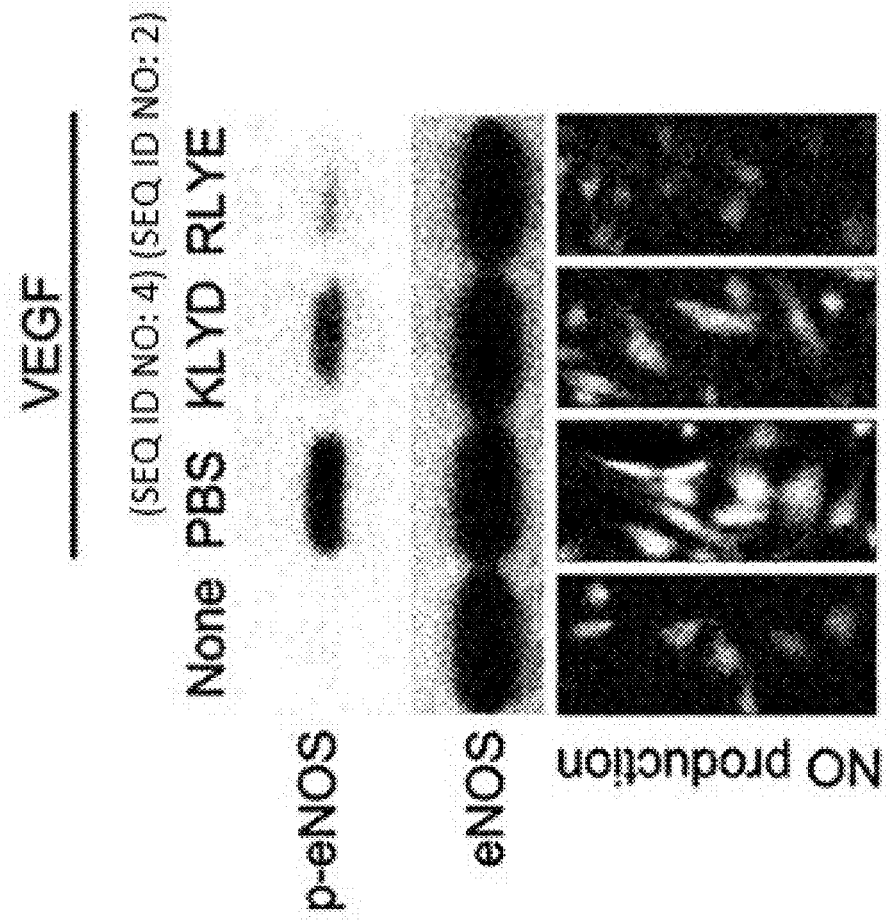

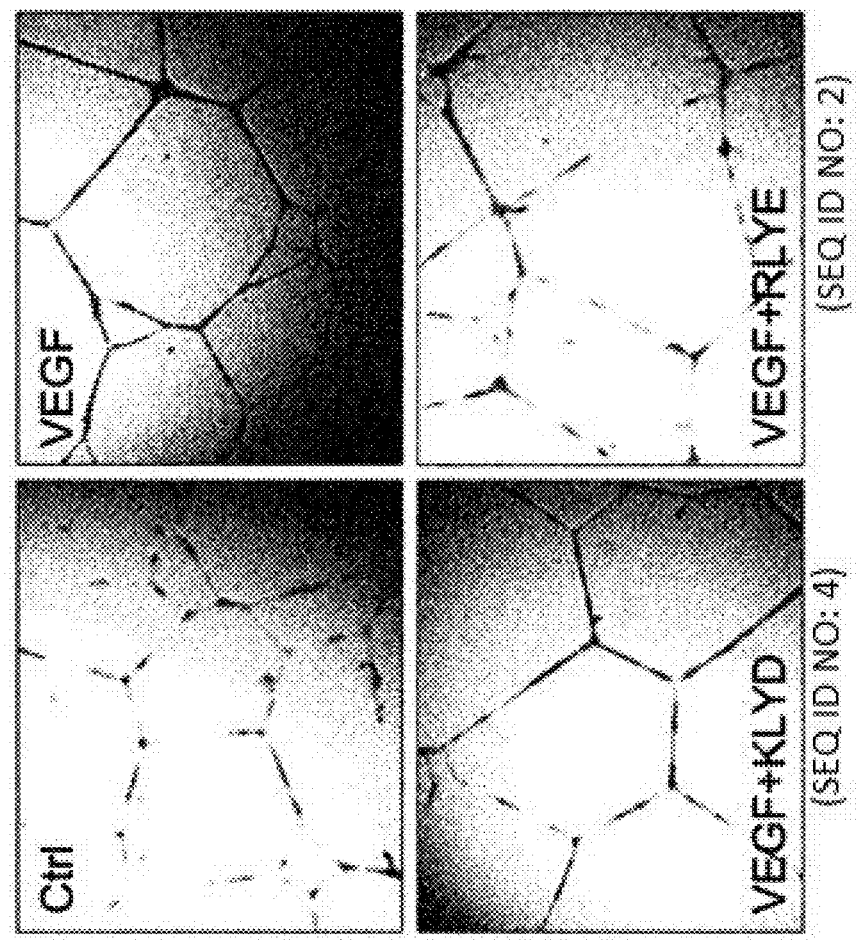

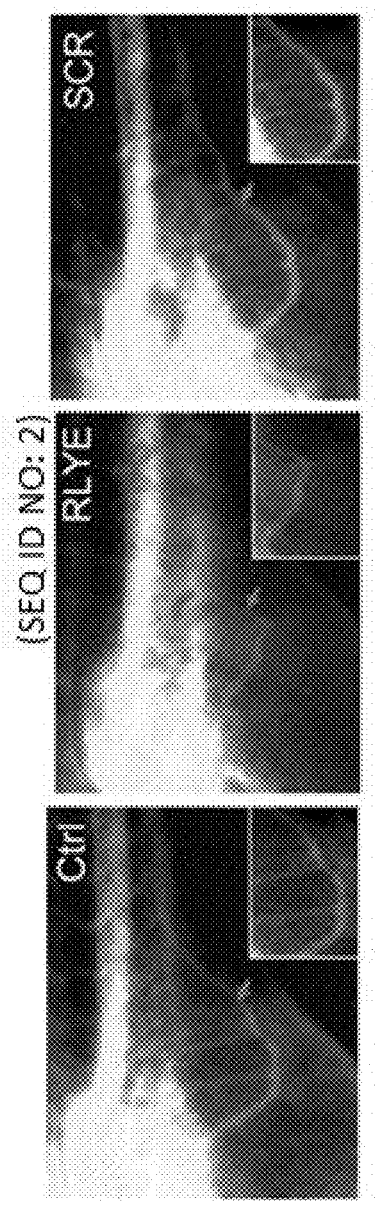
FIG. 4A
FIG. 4B

SEQUENCE LISTING

```
<160> NUMBER OF SEQ ID NOS: 13

<210> SEQ ID NO 1
<211> LENGTH: 4
<212> TYPE: PRT
```

```
<213> ORGANISM: Artificial Sequence
<220> FEATURE:
<223> OTHER INFORMATION: synthetic construct
<220> FEATURE:
<221> NAME/KEY: SITE
<222> LOCATION: (2)..(2)
<223> OTHER INFORMATION: Xaa is one of leucine, isoleucine, or valine
<220> FEATURE:
<221> NAME/KEY: SITE
<222> LOCATION: (3)..(3)
<223> OTHER INFORMATION: Xaa is tyrosine or phenylalanine

<400> SEQUENCE: 1

Arg Xaa Xaa Glu
  1

<210> SEQ ID NO 2
<211> LENGTH: 4
<212> TYPE: PRT
<213> ORGANISM: Artificial Sequence
<220> FEATURE:
<223> OTHER INFORMATION: synthetic construct

<400> SEQUENCE: 2

Arg Leu Tyr Glu
  1

<210> SEQ ID NO 3
<211> LENGTH: 4
<212> TYPE: PRT
<213> ORGANISM: Artificial Sequence
<220> FEATURE:
<223> OTHER INFORMATION: synthetic construct

<400> SEQUENCE: 3

Arg Val Tyr Glu
  1

<210> SEQ ID NO 4
<211> LENGTH: 4
<212> TYPE: PRT
<213> ORGANISM: Artificial Sequence
<220> FEATURE:
<223> OTHER INFORMATION: synthetic construct

<400> SEQUENCE: 4

Lys Leu Tyr Asp
  1

<210> SEQ ID NO 5
<211> LENGTH: 4
<212> TYPE: PRT
<213> ORGANISM: Artificial Sequence
<220> FEATURE:
<223> OTHER INFORMATION: synthetic construct

<400> SEQUENCE: 5

Lys Leu Tyr Glu
  1

<210> SEQ ID NO 6
<211> LENGTH: 4
<212> TYPE: PRT
<213> ORGANISM: Artificial Sequence
<220> FEATURE:
<223> OTHER INFORMATION: synthetic construct

<400> SEQUENCE: 6
```

Arg Leu Tyr Asp
1

<210> SEQ ID NO 7
<211> LENGTH: 4
<212> TYPE: PRT
<213> ORGANISM: Artificial Sequence
<220> FEATURE:
<223> OTHER INFORMATION: synthetic construct

<400> SEQUENCE: 7

Lys Leu Phe Asp
1

<210> SEQ ID NO 8
<211> LENGTH: 4
<212> TYPE: PRT
<213> ORGANISM: Artificial Sequence
<220> FEATURE:
<223> OTHER INFORMATION: synthetic construct

<400> SEQUENCE: 8

Lys Ile Tyr Asp
1

<210> SEQ ID NO 9
<211> LENGTH: 4
<212> TYPE: PRT
<213> ORGANISM: Artificial Sequence
<220> FEATURE:
<223> OTHER INFORMATION: synthetic construct

<400> SEQUENCE: 9

Lys Leu Trp Asp
1

<210> SEQ ID NO 10
<211> LENGTH: 4
<212> TYPE: PRT
<213> ORGANISM: Artificial Sequence
<220> FEATURE:
<223> OTHER INFORMATION: synthetic construct

<400> SEQUENCE: 10

Arg Leu Met Glu
1

<210> SEQ ID NO 11
<211> LENGTH: 4
<212> TYPE: PRT
<213> ORGANISM: Artificial Sequence
<220> FEATURE:
<223> OTHER INFORMATION: synthetic construct

<400> SEQUENCE: 11

Glu Tyr Leu Arg
1

<210> SEQ ID NO 12
<211> LENGTH: 4
<212> TYPE: PRT
<213> ORGANISM: Artificial Sequence
<220> FEATURE:
<223> OTHER INFORMATION: synthetic construct

<400> SEQUENCE: 12

Glu Tyr Leu Lys

```
<210> SEQ ID NO 13
<211> LENGTH: 4
<212> TYPE: PRT
<213> ORGANISM: Artificial Sequence
<220> FEATURE:
<223> OTHER INFORMATION: synthetic construct

<400> SEQUENCE: 13

Lys Leu Trp Glu
 1
```

TETRAPEPTIDE HAVING EFFECT OF INHIBITING VEGF-INDUCED ANGIOGENESIS AND USE THEREOF

CROSS-REFERENCE TO RELATED APPLICATION

This application claims priority to and the benefit of Korean Patent Application No. 10-2015-0110066, filed on Aug. 4, 2015, the disclosure of which is incorporated herein by reference in its entirety.

BACKGROUND

1. Field of the Invention

The present invention relates to a tetrapeptide for inhibiting VEGF-induced angiogenesis and a use thereof, and more particularly, to a peptide having the amino acid sequence of R-X1-X2-E (wherein X1 is leucine (L), isoleucine (I) or valine (V), and X2 is tyrosine (Y) or phenylalanine (F)) (SEQ ID NO: 1) for inhibiting angiogenesis or preventing, improving or treating cancer.

This research was supported by grants from the National Research Foundation of Korea (NRF) funded by the Ministry of Science, ICT and Future Planning (MSIP), Republic of Korea, in 2011 and 2013 [NRF-2011-0028790 and 2013M3A9B6046563]. This research has been supported by a grant of the Korea Health Technology R&D Project through the Korea Health Industry Development Institute (KHIDI), funded by the Ministry of Health & Welfare, Republic Korea (grant number: HI17C2273).

2. Discussion of Related Art

Angiogenesis is generated in various normal and pathological conditions, and refers to formation of new blood vessels from pre-existing vessels. Physiological conditions such as embryonic development, wound healing and formation of blood vessels are regulated by the balance between stimulators and inhibitors. However, physiological conditions inducing abnormal angiogenesis cause various diseases including tumor growth and metastasis, rheumatoid arthritis, diabetic retinopathy, etc.

Angiogenesis is usually induced by a sequential process including vascular endothelial cell activation, proliferation, migration, and tube formation, caused by various angiogenesis factors. Among the angiogenesis factors, vascular endothelial growth factor (VEGF) plays an important role in activating various signal transduction chain reactions to induce endothelial cell proliferation, migration and differentiation. Under the pathological conditions, VEGF induces abnormal angiogenesis, stimulates tumor growth and retinal cell growth and vascular leakage, resulting in tumor growth and metastasis and diabetic retinopathy. Therefore, using a VEGF antibody and a signal inhibitor, physiological activity and signal transduction chain reactions of VEGF may be inhibited, thereby controlling tumor angiogenesis and retinal angiogenesis. Angiogenesis-inhibiting treatment targeting VEGF or a VEGF receptor is a good strategy for pathological angiogenesis associated with human diseases.

Recently, some anti-angiogenesis antibodies, proteins and chemicals have been developed and clinically used to treat angiogenesis-associated diseases including tumors and diabetic retinopathy, but have therapeutic limitations such as side effects, non-specificity, low bioavailability, antigenicity and inappropriate pharmacokinetics. Generally, since small peptides have advantages such as mass production, low antigenicity, high solubility, specificity and bioavailability, they are suggested as excellent factors for drug development.

Therefore, the inventors conducted research to develop a peptide capable of effectively inhibiting angiogenesis induced by VEGF. It was confirmed that a peptide comprising the amino acid sequence of R-X1-X2-E (wherein X1 is leucine (L), isoleucine (I) or valine (V), and X2 is tyrosine (Y) or phenylalanine (F)) (SEQ ID NO: 1) exhibits a high inhibitory activity with respect to angiogenesis induced by VEGF, and can be very useful as a therapeutic agent for an angiogenesis-associated disease, particularly, cancer, and thus the present invention was completed.

PRIOR ART DOCUMENTS

Non-Patent Documents (Non-patent document 0001) G. Neufeld, T. Cohen, S. Gengrinovitch, Z. Poltorak, Vascular endothelial growth factor (VEGF) and its receptors, FASEBJ. 13 (1999) 9-22.

(Non-patent document 0002) J. Folkman, Angiogenesis in cancer, vascular, rheumatoid and other disease, Nat. Med. 1 (1995) 27-31.

(Non-patent document 0003) R. H. Adams, K. Alitalo, Molecular regulation of angiogenesis and lymphangiogenesis, Nat. Rev. Mol. Cell Biol. 8 (2007) 8464-8478.

(Non-patent document 0004) N. Ferrara, H. P. Gerber, J. LeCouter, The biology of VEGF and its receptors, Nat. Med. 9 (2003) 669-676.

(Non-patent document 0005) N. Ferrara, R. S. Kerbel, Angiogenesis as a therapeutic target, Nature 438 (2005) 967-74.

(Non-patent document 0006) H. Takahashi, M. Shibuya, The vascular endothelial growth factor (VEGF)/VEGF receptor system and its role under physiological and pathological conditions, Clin. Sci. (Lond) 109 (2005) 227-241.

(Non-patent document 0007) M. Shibuya, VEGF-VEGFR Signals in Health and Disease, Biomol. Ther. (Seoul) 22 (2014) 1-9.

(Non-patent document 0008) F. M. Yakes, J. Chen, J. Tan, K. Yamaguchi, Y. Shi, P. Yu, F. Qian, F. Chu, F. Bentzien, B. Cancilla, J. Orf, A. You, A. D. Laird, S. Engst, L. Lee, J. Lesch, Y. C. Chou, A. H. Joly, Cabozantinib (XL184), a novel MET and VEGFR2 inhibitor, simultaneously suppresses metastasis, angiogenesis, and tumor growth, Mol. Cancer Ther. 10 (2011) 2298-2308.

(Non-patent document 0009) D. J. Davidson, J. Wang, E. J. Gubbins, Novel antiangiogenic peptides, polypeptides angiogenesis encoding same and methods for inhibiting, International Patent WO 97/41824

(Non-patent document 0010) S. R. Wedge, D. J. Ogilvie, M. Dukes, J. Kendrew, R. Chester, J. A. Jackson, S. J. Boffey, P. J. Valentine, J. O. Curwen, H. L. Musgrove, G. A. Graham, G. D. Hughes, A. P. Thomas, E. S. Stokes, B. Curry, G. H. Richmond, P. F. Wadsworth, A. L. Bigley, L. F. Hennequin, ZD6474 inhibits vascular endothelial growth factor signaling, angiogenesis, and tumor growth following oral administration, Cancer Res. 62 (2002) 4645-4655.

(Non-patent document 0011) W. K. You, B. Sennino, C. W. Williamson, B. Falcon, H. Hashizume, L. C. Yao, D. T. Aftab, D. M. McDonald, VEGF and c-Met blockade amplify angiogenesis inhibition in pancreatic islet cancer, Cancer Res. 71(2011) 4758-4768.

(Non-patent document 0012) D. D. Hu-Lowe, H. Y. Zou, M. L. Grazzini, M. E. Hallin, G. R. Wickman, K. Amundson, J. H. Chen, D. A. Rewolinski, S. Yamazaki, E. Y. Wu, M. A. McTigue, B. W. Murray, R. S. Kania, P. O'Connor, D. R. Shalinsky, S. L. Bender, Nonclinical antiangiogenesis and antitumor activities of axitinib (AG-013736), an oral, potent, and selective inhibitor of vascular endothelial growth factor receptor tyrosine kinases 1, 2, 3, Clin. Cancer Res. 14 (2008)7272-7283.

(Non-patent document 0013) F. Hilberg, G. J. Roth, M. Krssak, S. Kautschitsch, W. Sommergruber, U. Tontsch-Grunt, P. Garin-Chesa, G. Bader, A. Zoephel, J. Quant, A. Heckel, W. J. Rettig, BIBF 1120: triple angiokinase inhibitor with sustained receptor blockade and good antitumor efficacy, Cancer Res. 68(2008) 4774-4782.

(Non-patent document 0014) J. C. Soria, A. Mauguen, M. Reck, A. B. Sandler, N. Saijo, D. H. Johnson, D. Burcoveanu, M. Fukuoka, B. Besse, J. P. Pignon, Systematic review and meta-analysis of randomised, phase II/III trials adding bevacizumab to platinum-based chemotherapy as first-line treatment in patients with advanced non-small-cell lung cancer, Ann. Oncol. 24 (2013) 20-30.

(Non-patent document 0015) S. J. Lee, S. Namkoong, Y. M. Kim, C. K. Kim, H. Lee, K. S. Ha, H. T. Chung, Y. G. Kwon, Y. M. Kim, Fractalkine stimulates angiogenesisby activating the Raf-1/MEK/ERK- and PI3K/Akt/eNOS-dependent signal pathways, Am. J. Physiol. Heart Circ. Physiol. 291 (2006) H2836-H2846.

(Non-patent document 0016) J. H. So, S. K. Hong, H. T. Kim, S. H. Jung, M. S. Lee, J. H. Choi, Y. K. Bae, T. Kudoh, J. H. Kim, C. H. Kim, 2010. Gicerin/Cd146 is involved in zebrafish cardiovascular development and tumor angiogenesis. Genes Cells 15 (2010) 1099-110.

(Non-patent document 0017) Y. Cao, A. Chen, S. S. A. An, R. W. Ji, D. Davidson, M. Llinas, Kringle 5 of plasminogen is a novel inhibitor of endothelial cell growth, J. Biol. Chem. 272 (1997) 22924-22928

(Non-patent document 0018) P. C. Lee, A. N. Salyapongse, G. A. Bragdon, L. L. Shears 2nd, S. C. Watkins, H. D. Edington, T. R. Billiar, Impaired wound healing and angiogenesis in eNOS-deficient mice, Am. J. Physiol. 277 (1999) H1600-1608.

(Non-patent document 0019) K. R. Kidd, B. M. Weinstein, Fishing for novel angiogenic therapies, Br. J. Pharmacol. 140 (2003) 585-594.

(Non-patent document 0020) S. Isogai, M. Horiguchi, B. M. Weinstein, The vascular anatomy of the developing zebrafish: an atlas of embryonic and early larval development. Dev. Biol. 230 (2001) 278-301.

(Non-patent document 0021) J. I. Greenberg, D. A. Cheresh, VEGF as an inhibitor of tumor vessel maturation: implications for cancer therapy, Expert Opin. Biol. Ther. 9 (2009) 1347-1356.

(Non-patent document 0022) A. Idbaih, F. Ducray, M. Sierra Del Rio, K. Hoang-Xuan, J. Y. Delattre, Therapeutic application of noncytotoxic molecular targeted therapy in gliomas: growth factor receptors and angiogenesis inhibitors, Oncologist 13 (2008) 978-992.

(Non-patent document 0023) K. M. Cook, W. D. Figg, Angiogenesis inhibitors: current strategies and future prospects, CA Cancer J. Clin. 60 (2010) 222-243.

(Non-patent document 0024) H. M. Verheul, H. M. Pinedo, Possible molecular mechanisms involved in the toxicity of angiogenesis inhibition, Nat. Rev. Cancer 7 (2007) 475-485.

(Non-patent document 0025) M. S. O'Reilly, L. Holmgren, Y. Shing, C. Chen, R. A. Rosenthal, M. Moses, W. S. Lane, Y. Cao, E. H. Sage, J. Folkman, Angiostatin: a novel angiogenesis inhibitor that mediates the suppression of metastases by a Lewis lung carcinoma, Cell 79 (1994) 315-328.

(Non-patent document 0026) G. S. Sheppard, M. Kawai, R. A. Craig, D. J. Davidson, S. M. Majest, R. L. Bell, J. Henkin, Lysyl 4-aminobenzoic acid derivatives as potent small molecule mimetics of plasminogen kringle 5, Bioorg. Med. Chem. Lett. 14 (2004) 965-966.

(Non-patent document 0027) Y. Wang, D. Fei, M. Vanderlaan, A. Song, Biological activity of bevacizumab, a humanized anti-VEGF antibody in vitro, Angiogenesis 7 (2004) 335-345.

SUMMARY OF THE INVENTION

Therefore, the present invention is directed to providing a peptide capable of effectively inhibiting angiogenesis induced VEGF, the peptide having a low risk with respect to side effects.

The present invention is also directed to providing a method of inhibiting angiogenesis, which includes: administering a pharmaceutically effective amount of the peptide to a subject.

The present invention is also directed to providing a method of preventing, improving or treating cancer, which includes: administering a pharmaceutically effective amount of the peptide to a subject.

According to an aspect of the present invention, the present invention provides a peptide for inhibiting angiogenesis, which comprises the amino acid sequence of R-X1-X2-E (SEQ ID NO: 1), in which X1 is L, I or V, and X2 is Y or F.

R: Arg, arginine
E: Glu, glutamic acid
L: Leu, leucine
I: Ile, isoleucine
V: Val, valine
Y: Tyr, tyrosine
F: Phe, phenylalanine The peptide for inhibiting angiogenesis of the present invention may comprise the amino acid sequence of R-L-Y-E (SEQ ID NO: 2) or R-V-Y-E (SEQ ID NO: 3).

The peptide of the present invention may effectively inhibit angiogenesis induced by vascular endothelial growth factor A (VEGF-A).

According to another aspect of the present invention, the present invention provides a method of inhibiting angiogenesis, which includes administering a pharmaceutically effective amount of the peptide to a subject.

According to still another aspect of the present invention, the present invention provides a method of preventing, improving or treating cancer, which includes administering a pharmaceutically effective amount of the peptide to a subject.

According to yet another aspect of the present invention, the present invention provides a peptide of preventing, improving or treating cancer, which includes a peptide for preventing, improving or treating cancer, which comprises the amino acid sequence of R-X1-X2-E (SEQ ID NO: 1), in which X1 is L, I or V, and X2 is Y or F.

The peptide for preventing, improving or treating cancer of the present invention may comprise the amino acid sequence of R-L-Y-E (SEQ ID NO: 2).

The peptide of the present invention may prevent, improve or treat cancer by effectively inhibiting angiogenesis induced by VEGF-A.

The peptide of the present invention may effectively prevent, improve or treat solid cancer among various types of cancer. Among types of the solid cancer, particularly, melanoma or colorectal cancer may be effectively prevented, improved or treated.

According to yet another aspect of the present invention, the present invention provides a method of preventing, improving or treating cancer, which includes administering a pharmaceutically effective amount of the peptide to a subject.

The method of the present invention may effectively prevent, improve or treat solid cancer among various types of cancer. Among types of the solid cancer, particularly, melanoma or colorectal cancer may be effectively prevented, improved or treated.

The peptide of the present invention may be used as a medicine or food for a human or animal, or feed for an animal.

Here, the peptide according to the present invention may be prepared according to a formulation standard for a conventional pharmaceutical agent or a formulation standard for a health supplement of the Ministry of Food and Drug Safety (MFDS).

The peptide of the present invention may be used as is or in the form of a pharmaceutically acceptable acid-addition salt or metal complex, for example, zinc, iron, etc., in the form of salts. More specifically, the acid-addition salt may be hydrogen chloride, hydrogen bromide, sulfate, phosphate, maleate, acetate, citrate, benzoate, succinate, malate, ascorbate or tartrate.

The peptide of the present invention may be diluted by mixing the oligopeptide with a pharmaceutically acceptable carrier, or may be loaded in a carrier formed in a container shape by a conventional method according to an administration route, a dosage form and the purpose of treatment.

When the carrier is used as a diluent, at least one carrier selected from the group consisting of saline, buffer, dextrose, water, glycerol, Ringer's solution, lactose, sucrose, calcium silicate, methyl cellulose, and ethanol may be prepared in the form of powder, granules, an injectable solution, syrup, liquid, tablets, suppositories, pessaries, salve, cream or an aerosol for oral administration or parenteral administration. However, the carrier is not limited to the above-described types of carriers. Here, the parenteral administration refers to rectal, intravenous, peritoneal, muscular, intraarterial, percutaneous or nasal administration, or inhalation of an effective component, excluding oral administration.

As a filler, an anti-coagulant, a lubricant, a wetting agent, a flavoring agent, an emulsifier or a preservative is further added to the above-prepared dosage form, and after being administered to a mammal, the composition can be prepared to provide fast, sustained or delayed release of the active component. In addition, dosage may be regulated by a patient's condition, administration route and administration type without limitation, and apparently used in various ranges by those of ordinary skill in the art according to symptoms. Usually, it is determined that the peptide of the present invention is able to be continuously or intermittently administered daily with an experimentally effective amount of approximately 0.5 to 1.0 mg per kg of a body weight.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIGS. 1A, 1B, and 1C show effects of various candidate peptide groups on proliferation and migration of endothelial cells (FIG. 1A: amino acid sequences of 10 peptides used in experiments, FIG. 1B: effects of peptides on inhibiting the proliferation of vascular endothelial cells (from [3H]-thymidine incorporation assay), FIG. 1C: effects of peptides on inhibiting endothelial cell migration, graph value: mean±standard deviation (n>3), for VEGF only-treated group, *P<0.05, **P<0.01);

FIGS. 2A, 2B, 2C, 2D, 2E and 2F are an experimental result of the effects of peptides on ERK phosphorylation, proliferation and migration of endothelial cells, and NO production (FIG. 2A: effects of peptides on ERK phosphorylation, FIG. 2B: effects of peptides on inhibition of proliferation of endothelial cells per concentration (from [3H]-thymidine incorporation assay), FIG. 2C: effects of KLYD (SEQ ID NO: 4) and RLYE (SEQ ID NO: 2) peptides on inhibition of migration of vascular endothelial cells (from hematoxylin and eosin (H&E) staining), FIG. 2D: effects of KLYD (SEQ ID NO: 4) and RLYE (SEQ ID NO: 2) peptides on inhibition of migration of vascular endothelial cells per concentration, FIG. 2E: effects of KLYD (SEQ ID NO: 4) and RLYE (SEQ ID NO: 2) peptides on inhibition of NO production, FIG. 2F: analysis of NO production levels of KLYD (SEQ ID NO: 4) and RLYE (SEQ ID NO: 2) peptides, graph values of FIG. 2D and FIG. 2F: mean±standard deviation (n>3), for VEGF only-treated group, *P<0.05, **P<0.01);

FIGS. 3A and 3B show the effects of peptides on tube formation of endothelial cells (FIG. 3A: effects of KLYD (SEQ ID NO: 4) and RLYE (SEQ ID NO: 2) peptides on inhibition of tube formation using Matrigel, FIG. 3B: graph showing the above result, graph value: mean±standard deviation (n>3), for VEGF only-treated group, *P<0.05, **P<0.01);

FIGS. 4A, 4B, 4C, and 4D show the effects of an RLYE (SEQ ID NO: 2) peptide on angiogenesis in a zebrafish model (FIG. 4A and FIG. 4B: effects on inhibition of subintestinal vessel (SIV) formation, FIG. 4C and FIG. 4D: effects on inhibition of intersegmental vessel (ISV) formation);

DETAILED DESCRIPTION OF EXEMPLARY EMBODIMENTS

Figure 1B:
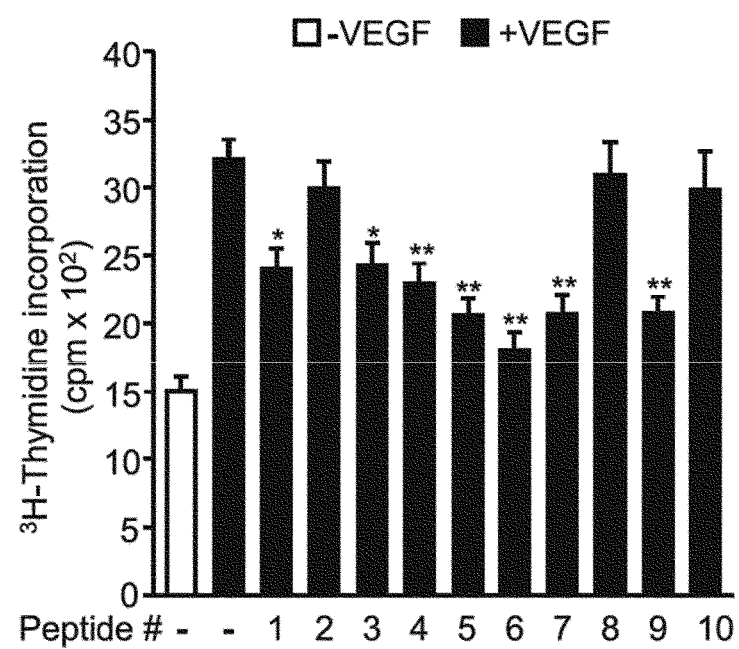

Hereinafter, the present invention will be described in further detail with reference to examples. The examples will be provided to describe the present invention, and it should not be interpreted that the scope of the present invention is limited by the following examples.

<Confirmation of Anti-Angiogenic and Anticancer Effects of Peptide>

1. Experimental Procedures 1-1. Cell Culture

Human umbilical vein endothelial cells (HUVECs) were cultured in M199 medium, and during experiments, the cells were always used at passages 2 to 7. Meanwhile, mouse melanoma cells (B16F1 and B16F10) and human colorectal tumor cells (HCT116) were cultured in RPMI media supplemented with 10% FBS, 1 mM sodium pyruvate, 10 mM 4-(2-hydroxyethyl)-1-piperazineethanesulfonic acid and 100 U/ml penicillin-streptomycin, and human multiple myeloma cells (IM-9 and RPMI 8226) were cultured in RPMI-1640 media. All of the cells were cultured at 37° C. with 5% $CO_2$ in a humidified incubator.

1-2. Experimental Animals

A 7-week-old male mouse C57BL/6J, a thymus-eliminated nude mouse and a Sprague-Dawley were used, and grown on a standard ad libitum diet in a sterilized air current rearing equipment. Animal testing was conducted under the guidelines of the animal ethics committee of Kangwon University. Also, the animal testing was followed by the guidelines for the care and use of laboratory animals published by the US National Institutes of Health (NIH Publication, 8th Edition, 2011).

1-3. In Vitro Angiogenesis Assay

Angiogenic activity was determined by measuring cell proliferation, migration and tube formation. HUVEC proliferation was analyzed by a [3H]-thymidine incorporation assay. The HUVECs were seeded in a 24-well plate coated with gelatin at a density of $2 \times 10^4$ cells/well. The cells were incubated for 24 hours to be attached to the plate, washed twice with M199 medium, and incubated in 1% FBS-containing M199 medium for 6 hours. The HUVECs were stimulated with various concentrations of tetrapeptides for 30 minutes, and with 10 ng/ml of VEGF for 24 hours. Subsequently, 0.5 µCi/ml of [3H]thymidine was added for a 6-hour reaction. 3H-labeled polymer DNA was evaluated with a liquid scintillation counter.

HUVEC migration was analyzed using a transwell plate equipped with a 6.5-mm-diameter polycarbonate filter (8-µm pore size). A lower surface of the filter was coated with 10 µg of gelatin. Fresh VEGF-containing M199 medium (1% FBS) was placed in lower wells. Following incubation with various concentrations of tetrapeptides at room temperature for 30 minutes, HUVECs ($1 \times 10^6$ cells/ 100 µl) were placed in upper wells. The cells were incubated at 37° C. in a constant temperature and humidity chamber for 4 hours. The migrated cells were stained with hematoxylin and eosin, and quantified under an optical microscope.

Tube formation of HUVECs was examined using growth factor-reduced Matrigel (hereinafter, referred to as "Matrigel"). 250 µl of Matrigel (10 mg protein/ml) was placed in a 24-well plate to allow polymerization for 30 minutes at 37° C. Following incubation in M199 (1% FBS) medium for 6 hours, the HUVECs were transferred to the Matrigel at a density of $2 \times 10^5$ cells/well, and then incubated with VEGF (10 ng/ml) alone or in combination with peptides (0.15 nM) at 37° C. for 20 hours. The tube formation was examined under a reverse phase-contrast microscope, and visualized with Image-Pro Plus version 4.5 (Media Cybernetics, San Diego, Calif.). Five samples were randomly selected to measure and quantify a length of the tube formed above.

1-4. Ex Vivo and In Vivo Angiogenesis Assays

An aortic ring sprouting assay was performed by a method modified based on previous research. A 1-mm-thick aortic ring prepared from a Sprague-Dawley rat (7-week-old male) was placed in a 96-well plate coated with 120 µl of Matrigel, sealed with 50 µl of Matrigel, and incubated with RLYE (SEQ ID NO: 2) (0.3 nM) or VEGF (20 ng/ml) in a total of 200 µl of a serum-free medium. Blood vessels newly formed at day 6 were fixed, microvascular formation was observed under a phase-contrast microscope, and angiogenesis was quantified with Image Jsoftware available at NIH website, rsb.info.nih.gov/ij.

For a chick chorioallantoic membrane (CAM) analysis, fertilized eggs were incubated for 3 days, and a window was made in the same manner as used in the previous research (18). The window (with a diameter of about 3 cm) was made by removing a shell and an inner layer of the shell, and the exposed part was sealed with cellophane tape. The eggs were stood upright at 37° C. in an incubator (with a humidity of 55 to 60%) and were incubated for 3 days. A Thermanox disc containing 10 µl of a salt-free solution containing RLYE (SEQ ID NO: 2) (0.75 nM) alone or in combination with VEGF (50 ng/ml) was gently placed on a CAM that had been incubated for 10 days. After 72-hour incubation, blood vessels formed above were stained by injecting 1 ml of a 10% intralipose (fat emulsion) solution right under the CAM. The stained blood vessels were photographed using a Nikon digital camera, and the number of blood vessels newly formed around the disc was counted.

Formation of new blood vessels was examined by intravital fluorescence microscopy. A C57BL/6J mouse was anesthetized, and then a titanium-made imaging window was installed between the skin and an abdominal wall by surgery. 100 µl of Matrigel containing RLYE (SEQ ID NO: 2) (1.5 nM) alone or in combination with VEGF (100 ng) was injected into an inner space between the skin and abdominal walls of the window. Four days later, 50 µl of dextran (MW 250 kDa) labeled with 25 mg/ml of FITC was injected into the caudal vein, and then formation of new blood vessels was observed under a Zeiss Axiovert 200M microscope (Carl Zeiss). A vascular length density of the FITC-labeled dextran-perfuse blood vessels per observation area (mm/mm2) was calculated.

1-5. Western Blotting Analysis

Cells were lyzed in RIPA buffer, and 50 µg of proteins were isolated by SDS-PAGE and then transferred to a PVDF membrane. The membrane was reacted with an antibody with respect to a target protein for 2 hours. The membrane was washed twice and reacted with a horseradish peroxidase-conjugated antibody, and then an amount of the target proteins was assessed with an enhanced chemiluminescence system.

1-6. Evaluation of Nitrogen Monoxide (NO) Production

An NO amount produced in HUVECs was evaluated with DAF-FM diacetate. HUVECs were reacted with peptides (0.15 nM) and VEGF (10 ng/ml) for 4 hours, and incubated with DAF-FM diacetate (5 µM) in a CO2 constant temperature incubator, and the amount of NO produced in the cells was measured under a confocal microscope.

1-7. Zebrafish angiogenesis assay

An adult zebrafish and an embryo were grown and maintained in a standard laboratory environment, and a zebrafish experiment was conducted according to the protocols approved by the animal ethics committee of Chungnam National University. To analyze angiogenesis, at 48 hours post fertilization (hpf), the embryo was anesthetized with tricaine (MS-222, 0.02%, embryo buffer), a peptide was administered, and FITC-dextran (2,000 kDa, Sigma) was further injected. A blood vessel image was obtained with a Leica DM5000B system at 72 hpf. As a probe for whole mount in situ hybridization, digoxigenin (DIG)-labeled RNA prepared by a cad5 (NM_001003983) gene was used. Meanwhile, a peptide was injected into the 18-hpf embryo collected at 25 hpf, fixed with 4% paraformaldehyde, washed with PBS (in 0.1% Tween20), and hybridized with DIG-labeled riboprobes (hybridization buffer). Subsequently, the resulting product was reacted with an alkaline phosphatase (AP)-conjugated anti-DIG antibody. Following reaction with an AP staining solution, a staining status was observed and visualized under a microscope (Leica, MZ-16).

1-8. Fluorescence-Activated Cell Sorting (FACS) Analysis

HUVECs were cultured in a 60-mm culture plate for 24 hours. The cells were isolated from the plate with 5 mM EDTA-containing phosphate-buffered saline (PBS), washed with PBS three times, and suspended in 2% FBS/0.1% bovine serum albumin-containing PBS. Afterward, before or after the reaction with FITC-conjugated RLYE (SEQ ID NO: 2) (15 nM), the cells were treated with VEGF (100 ng/ml), stored on ice for 30 minutes, fixed in 2% paraformaldehyde, and assessed with a fluorescence activated cell sorter (FACS Calibur, Becton Dickinson) by flow cytometry.

1-9. VEGFR Pull-Down Assay Using Biotin-Labeled RLYE (SEQ ID NO: 2)

HUVECs were lysed in a pull-down buffer [50 mM Tris-HCl (pH 8.0), 150 mM sodium chloride, 1.0% NP-40, 0.5% sodium deoxycholate and 0.1% SDS]. A lysate (500 mg of proteins) was reacted with biotin-labeled RLYE (SEQ ID NO: 2) (0.15 or 1.5 nM) for 1 hour, and reacted with streptavidin-agarose beads (20 ml) at 4° C. for 1 hour. RLYE (SEQ ID NO: 2)-binding proteins were isolated from the cell lysate through centrifugation, washed, and then boiled for 10 minutes. The bead-binding proteins were isolated by SDS-PAGE, and immunoblotting was performed with an antibody with respect to VEGFR-2 or VEGFR-1.

1-10. Mouse Melanoma (B16F1) and Human Colorectal Tumor (HCT116) Animal Models 100 µl each of 2×106 B16F1 mouse melanoma cells and 1×107 HCT116 human colorectal tumor cells were subcutaneously injected into the left side of a C57BL/6J mouse and a nude mouse. After a tumor volume reached at least 50 to 70 mm3 (taking about 7 days), saline or RLYE (SEQ ID NO: 2) (0.5 or 1.0 mg/kg) was peritoneally injected daily into the mice. A tumor size was two-dimensionally measured with calipers. A tumor volume (mm3) was calculated by a formula of 2 (width)×0.52 (length). Following homogenization of tumor tissue with PBS and centrifugation (at 12,000×g for 5 min), a hemoglobin-containing supernatant was extracted to be used in analysis with Drabkin's reagent (Sigma). A hemoglobin level was measured by a cyanmethemoglobin method, and the amount of hemoglobin per gram of the tumor was calculated.

1-11. Tumor Metastasis Experiment Model

1×105 B16F10 mouse melanoma cells were injected into the caudal vein in the C57BL/6J mouse, and 1 mg/kg (100 µl) of RLYE (SEQ ID NO: 2) was peritoneally injected daily for 3 weeks. The lung was extracted and washed with Dulbecco's PBS, fixed in a 4% paraformaldehyde solution overnight, and the number of tumor metastasis shown on the entire surface of the lung was counted under a stereoscopic microscope.

1-12. Surface Plasmon Resonance (SPR) Assay

Binding dynamics and affinity of RLYE (SEQ ID NO: 2) to rhVEGFR-2 were evaluated with BIAcore AB (Sweden). A carboxymethylated dextran biosensor chip (CM5, BIAcore AB) was activated with 1-ethyl-3-(3-dimethylaminopropyl)carbodiimide and N-hydroxysuccinimide according to the manufacturer's manual. The rhVEGFR-2 (1 ng/μl, 10 mM Hepes, 150 mM NaCl, 3 mM EDTA, 0.005% Tween-20-containing HBS-EP buffer) was injected over the activated CM5 chip for fixation. Various concentrations of an RLYE (SEQ ID NO: 2) solution was injected over the rhVEGFR-2-fixed center chip with a flow rate of 25 μl/min, and binding and non-binding characteristics between RLYE (SEQ ID NO: 2) and the rhVEGFR-2 were analyzed. The peptide bonds were measured in arbitrary response units, and after the injection of each sample (120 sec), the HBS-EP buffer was passed over a sensor surface to monitor dissociation. The equilibrium dissociation constant (Kd) was derived to a fixing step-combined model.

1-13. Immunostaining Assay

HUVECs were incubated on a cover glass coated with 2% gelatin, and then incubated with FITC-RLYE (SEQ ID NO: 2) (100 ng/ml) after being treated with VEGF-A (10 ng/ml) for 30 minutes or not treated. The cells were fixed in 3.7% formaldehyde for 30 minutes, treated with 0.2% TritonX-100-containing PBS, and reacted with a 3% goat serum and 0.05% Tween-20-containing PBS blocking solution. The cells were reacted with a PECAM-1 antibody at room temperature for 2 hours, washed with PBS, and reacted with a TRITC-conjugated secondary antibody at room temperature for 90 minutes. Samples were observed under a confocal microscope.

Tumor tissue was fixed in 10% formalin, and inserted into paraffin. A slide was prepared from a tissue section, embedded in xylene to remove the paraffin, and rehydrated with 100%, 95%, 80% and 70% ethanol (EtOH) in s stepwise manner. Afterward, the slide was washed with deionized water multiple times at room temperature. To inhibit an intracellular peroxidase activity, the section was reacted in 0.3% hydrogen peroxide-containing methanol for 15 minutes, washed with PBS three times, reacted in 3% goat serum-containing PBS at room temperature for 2 hours, and reacted with a PECAM-1 antibody overnight at 4° C. The tissue section slide was washed with PBS three times, and reacted with a TRITC-conjugated secondary antibody for 1 hour. In addition, the tumor tissue section was also reacted with FITC-isolectin B4 (5 mg/ml; Vector Laboratories) for 1 hour. The tissue section was washed with PBS three times, and treated with a Permount solution to make a slide, followed by observation of tumor blood vessels under a fluorescence microscope.

1-14. Docking Simulations

A coordinate structure of RLYE (SEQ ID NO: 2) peptides was generated with Chimera software, and blind docking of RLYE (SEQ ID NO: 2) with respect to VEGFR-2 (PDB ID 2X1W) extracted from a VEGF/VEGFR-2 complex was performed. A 0.15 Å grid box was set up to encompass entire VEGFR molecules with an Autodock 4.2 program. To describe multiple-rotatable bonds in the RLYE (SEQ ID NO: 2) peptide, an energy evaluation number was raised to $5 \times 10^7$. Blind docking was performed 1000 times using a Lamarckian genetic algorithm. The Chimera software was used for a conformational image.

1-15. Statistical Analysis

Based on at least three independent tests, test results were expressed as mean±standard deviation. For statistical significance, the Student's t test was used to analyze data to compare the difference among multiple groups. Data when P-value was less than 0.05 were determined statistically significant.

2. Experimental Results 2-1. Selection of Anti-Angiogenic Candidate Peptides

Figure 1C:
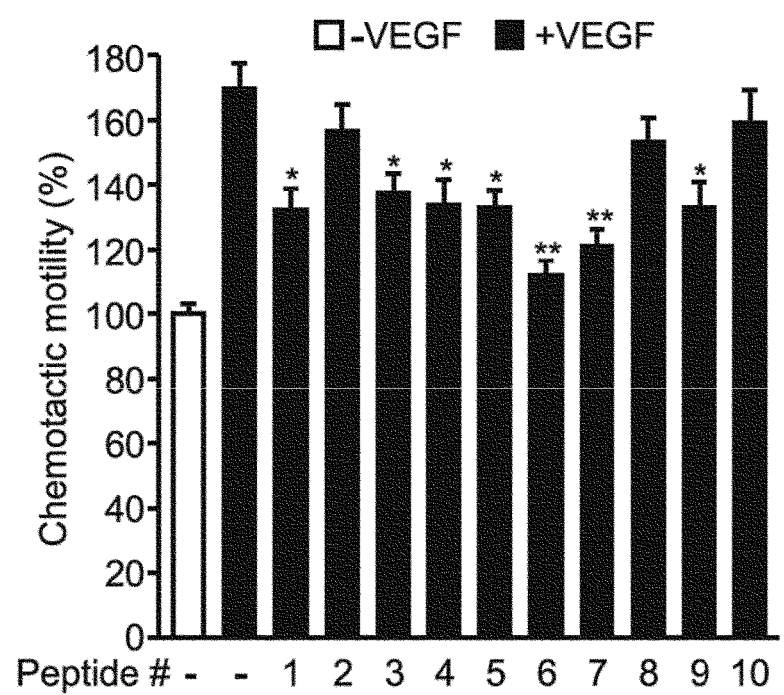

Ten tetrapeptides were synthesized based on an amino acid sequence and chemical properties of the tetrapeptide KLYD (SEQ ID NO: 4) derived from plasminogen kringle domain 5. To verify angiogenesis regulatory efficiency under cell culture conditions that had been generally used, it was first confirmed that the synthesized tetrapeptide inhibited HUVEC proliferation. As expected, the KLYD (SEQ ID NO: 4) peptide used as a positive control significantly inhibited the HUVEC proliferation induced by VEGF. Among 9 other peptides, KLYE (SEQ ID NO: 5), RLYE (SEQ ID NO: 2), RLYD (SEQ ID NO: 6) and RVYE (SEQ ID NO: 3) effectively inhibited the VEGF-induced HUVEC proliferation, compared with the control, KLYD (SEQ ID NO: 4). Meanwhile, KLFD (SEQ ID NO: 7) and KIYD (SEQ ID NO: 8) exhibited an inhibitory effect similar to the positive control. However, KLWD (SEQ ID NO: 9), RLME (SEQ ID NO: 10) and EYLR (SEQ ID NO: 11) (scrambled peptide against RLYE (SEQ ID NO: 2)) did not exhibit a significant inhibitory effect on the VEGF-induced HUVEC proliferation. Meanwhile, the inhibitory effect of all tetrapeptides on HUVEC migration induced by VEGF was similar to that on the HUVEC proliferation (see FIG. 1C). The tetrapeptides KLYE (SEQ ID NO: 5), RLYE (SEQ ID NO: 2), RLYD (SEQ ID NO: 6) and RVYE (SEQ ID NO: 3) were considered factors potential to an angiogenesis inhibiting activity, compared with the control, KLYD (SEQ ID NO: 4). Such a result demonstrates that, in the amino acid sequence of the tetrapeptide, the first amino acid, R (Arg, arginine), and the fourth amino acid, E (Glu, glutamic acid), are important, for the second amino acid, a hydrophobic amino acid such as L (Leu, leucine), I (Ile, isoleucine) or V (Val, valine) is important, and for the third amino acid, a hydrophobic amino acid such as Y (Tyr, tyrosine) or F (Phe, phenylalanine) is important.

2-2. Anti-Angiogenic Peptide RLYE (SEQ ID NO: 2)

Figure 2A:
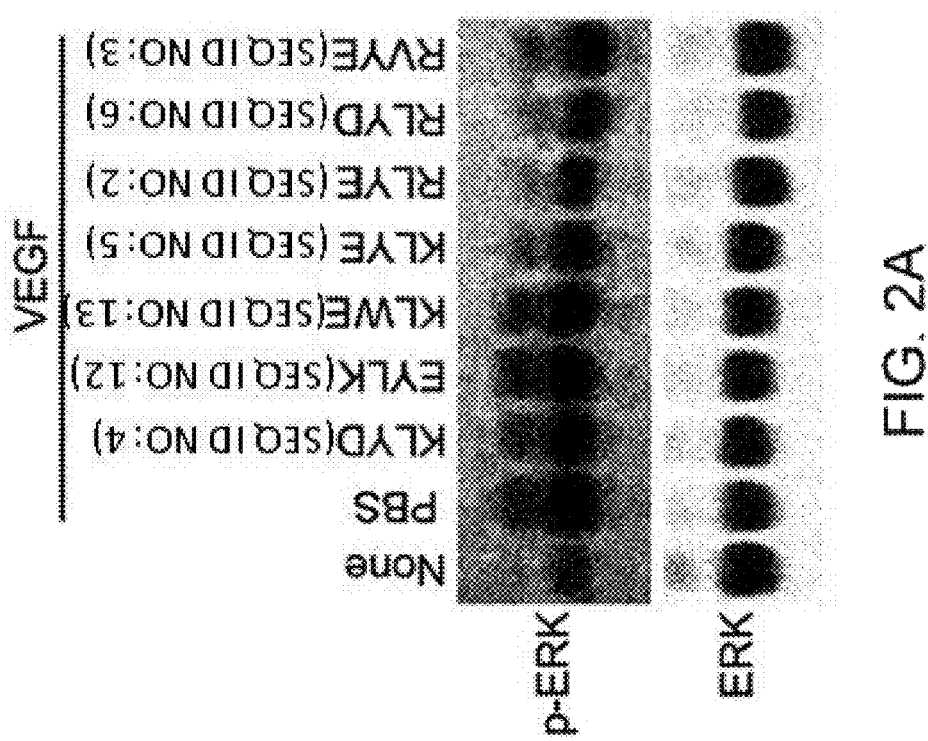
Figure 2B:
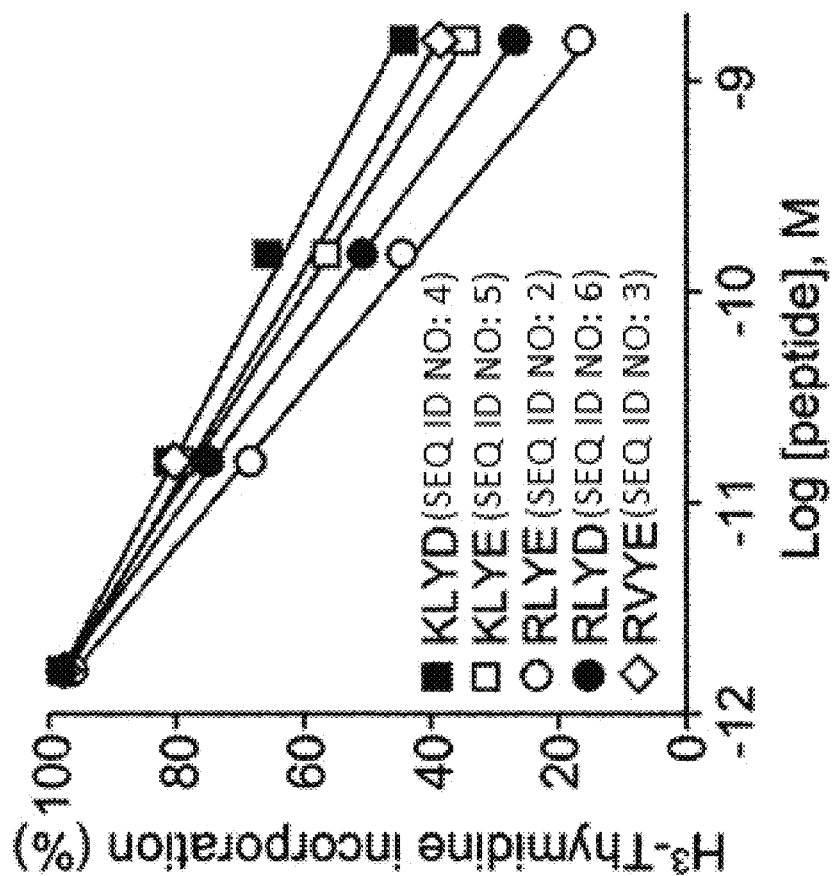
Figure 2C:
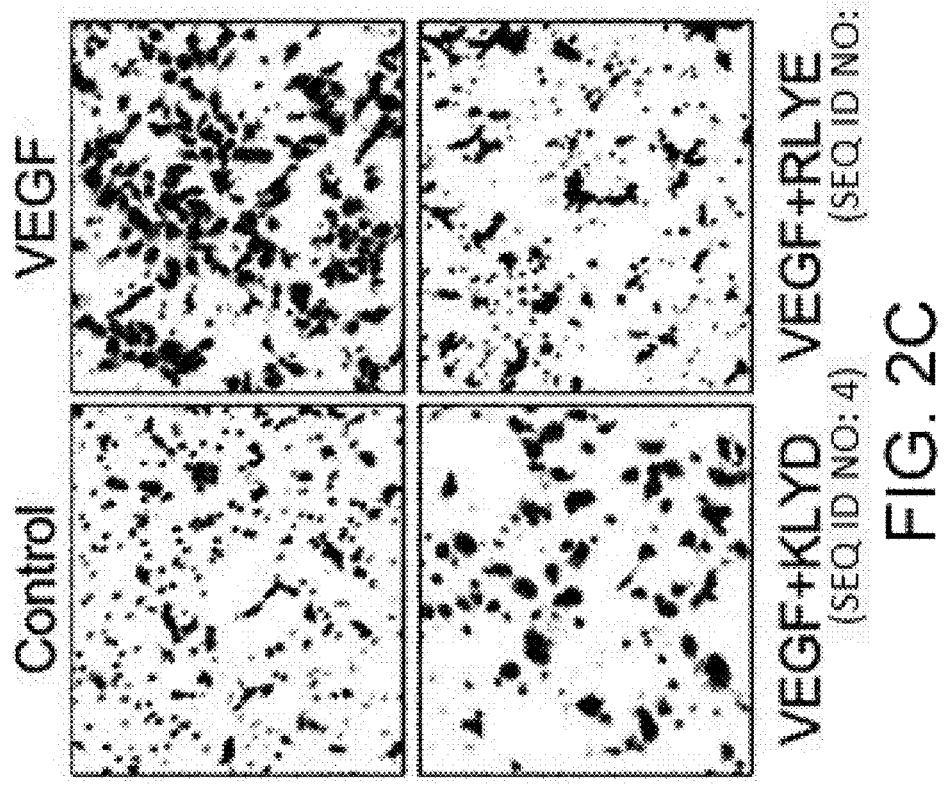
Figure 2D:
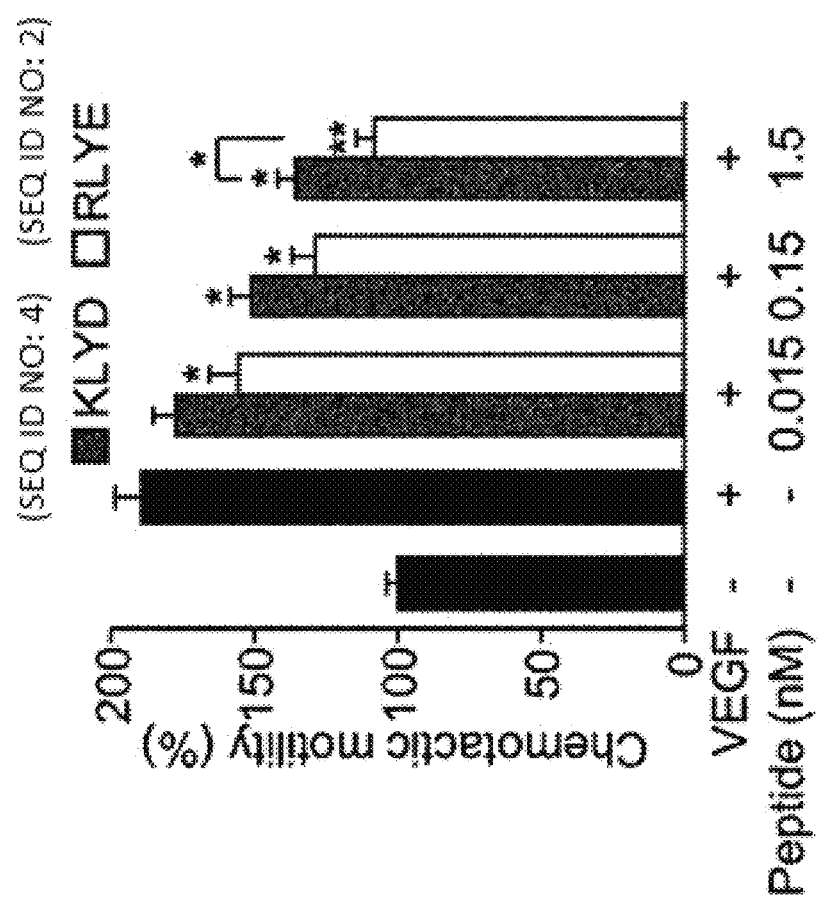
Figure 2F:
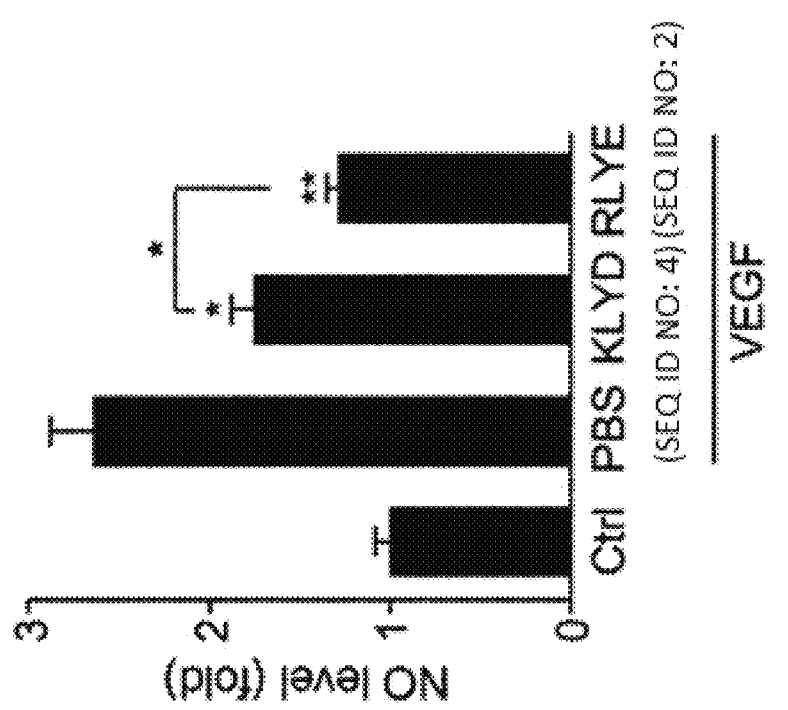

The effects of four tetrapeptides KLYE (SEQ ID NO: 5), RLYE (SEQ ID NO: 2), RLYD (SEQ ID NO: 6) and RVYE (SEQ ID NO: 3) on phosphorylation of ERK, which is a main factor for VEGF-induced HUVEC signaling, were investigated. The KLYE (SEQ ID NO: 5), RLYE (SEQ ID NO: 2), RLYD (SEQ ID NO: 6) and RVYE (SEQ ID NO: 3) more effectively inhibited the VEGF-induced ERK phosphorylation than the control KLYD (SEQ ID NO: 4), and among the above peptides, RLYE (SEQ ID NO: 2) exhibited the highest inhibitory effect (see FIG. 2A). Also, the VEGF-induced HUVEC proliferation was expressed as IC50 value. The IC50 values of the KLYE (SEQ ID NO: 5), RLYE (SEQ ID NO: 2), RLYD (SEQ ID NO: 6) and RVYE (SEQ ID NO: 3) were 0.30, 0.08, 0.14 and 0.39, respectively, and the IC50 value of RLYE (SEQ ID NO: 2) was 10-fold lower than that of the control KLYD (SEQ ID NO: 4) (0.79 nM) (see FIG. 2B). An effect of a change in RLYE (SEQ ID NO: 2) content (concentration) on VEGF-induced HUVEC migration was examined. RLYE (SEQ ID NO: 2) concentration-dependently inhibited the VEGF-induced HUVEC migration, and the IC50 value was identified 0.06 nM (see FIGS. 2C and 2D). NO synthesized by an NO synthase (eNOS) expressed in HUVECs plays an important role in the function and formation of blood vessels. Accordingly, an influence of RLYE (SEQ ID NO: 2) on NO production in the HUVECs was investigated. RLYE (SEQ ID NO: 2) effectively inhibited the VEGF-induced NO production in the HUVECs, and had a higher inhibitory effect than the control KLYD (SEQ ID NO: 4) (FIGS. 2E and 2F). Such results demonstrate that RLYE (SEQ ID NO: 2) exhibits the most excellent inhibitory effect on VEGF-induced angiogenesis, compared with the other 9 peptides.

Figure 3B:
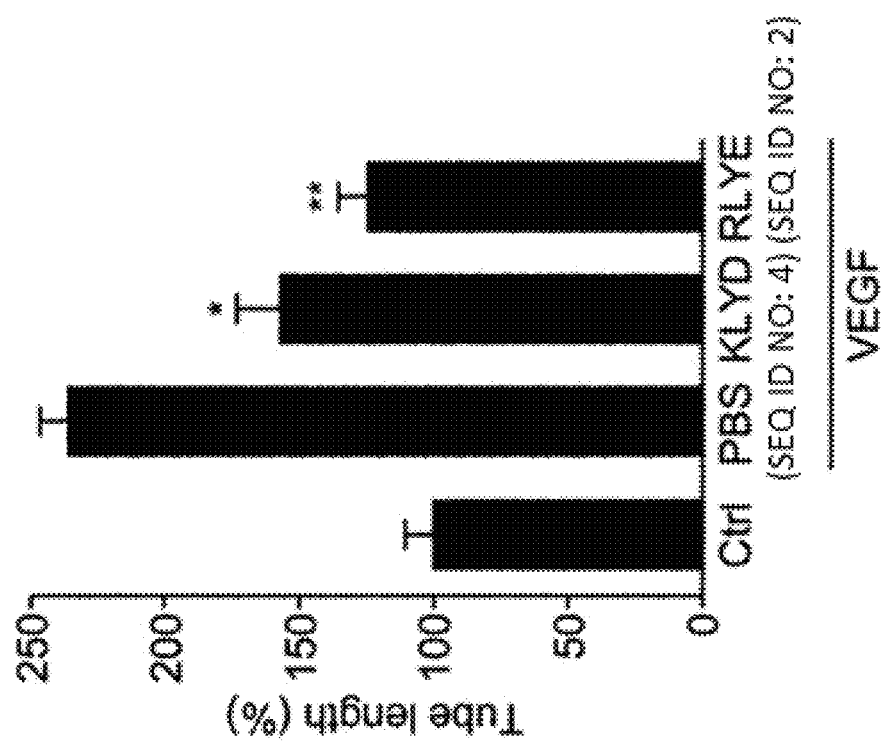

2-3. Inhibitory Effects on VEGF-Induced Angiogenesis Signaling and Tube Formation VEGF stimulates proliferation and migration of HUVECs, and morphological differentiation associated with the tube formation in HUVECs. Therefore, an effect of RLYE (SEQ ID NO: 2) on the tube formation in the HUVECs was investigated using two-dimensional Matrigel. VEGF stimulated the tube formation of the HUVECs, and when RLYE (SEQ ID NO: 2) is treated, the width and length of a tube of the HUVEC, which was formed by induction of VEGF, were effectively regulated. The RLYE (SEQ ID NO: 2) exhibited a much higher inhibitory effect on the tube formation than KLYD (SEQ ID NO: 4) (FIGS. 3A and 3B). Such a result demonstrates that RLYE (SEQ ID NO: 2) is able to more strongly inhibit VEGF-induced angiogenesis.

2-4. Inhibitory Effect on Angiogenesis in Zebrafish Model

Figure 4C:
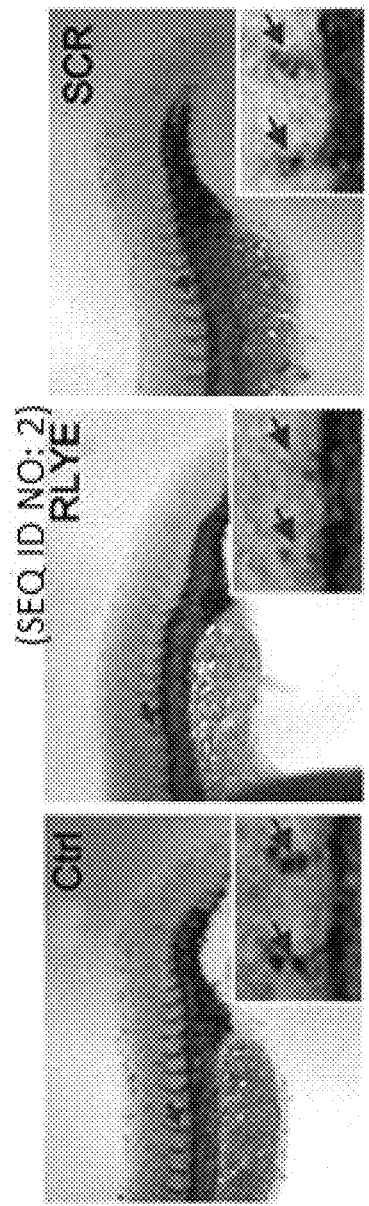
Figure 4D:
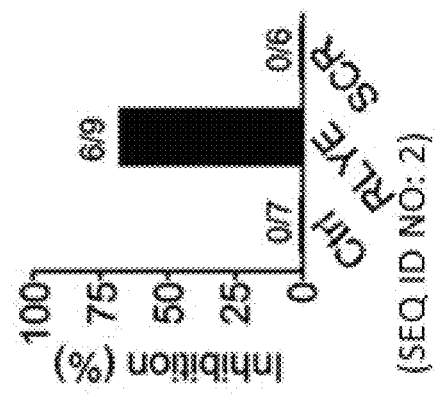

An angiogenesis process and anatomical blood vessel patterns are well conserved in all vertebrates as well as zebrafish. Therefore, a research model using zebrafish has been used in developing angiogenesis and function regulatory factors or drugs, and also used in research on regulating blood vessel development. For this reason, an effect of RLYE (SEQ ID NO: 2) on angiogenesis was investigated in the zebrafish model. When an RLYE (SEQ ID NO: 2) peptide was administered to fertilized eggs of the zebrafish, the formation of subintestinal vessels (SIV) was considerably inhibited, whereas a scrambled peptide used as a control did not affect the SIV formation (see FIGS. 4A and 4B). Also, when RLYE (SEQ ID NO: 2) was injected, the formation of intersegmental vessels (ISV) was obviously inhibited, whereas the scrambled peptide did not affect the ISV formation (see FIGS. 4C and 4D). Such experimental results show that RLYE (SEQ ID NO: 2) inhibits angiogenesis in a zebrafish model.

2-5. Inhibitory Effect on Ex Vivo and In Vivo Angiogenesis

Figure 5A:
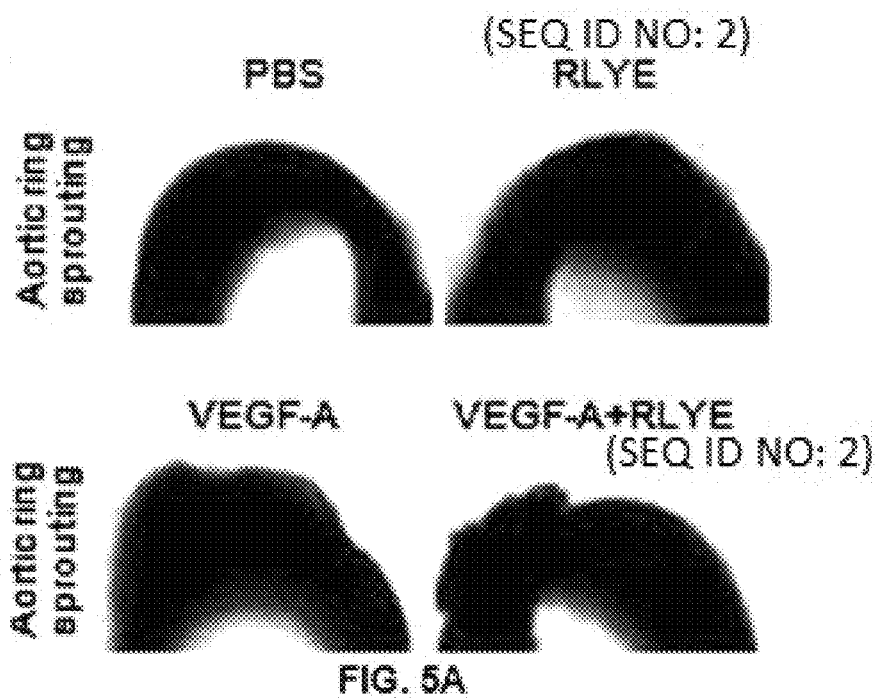
FIGS. 5A, 5B, 5C, 5D, 5E, and 5F show the effects of an RLYE (SEQ ID NO: 2) peptide on ex vivo and in vivo angiogenesis (FIG. 5A and FIG. 5B: effects of RLYE (SEQ ID NO: 2) peptide on inhibition of aortic ring angiogenesis (ex vivo), FIG. 5C and FIG. 5D: effects of RLYE (SEQ ID NO: 2) peptide on a chick chorioallantoic membrane (CAM) (in vivo), FIG. 5E and FIG. 5F: effects of RLYE (SEQ ID NO: 2) peptide on inhibition of angiogenesis using Matrigel implantation (in vivo), graph value: mean±standard deviation (n>6), for VEGF-A only-treated group, *P<0.05, **P<0.01)
Figure 5B:
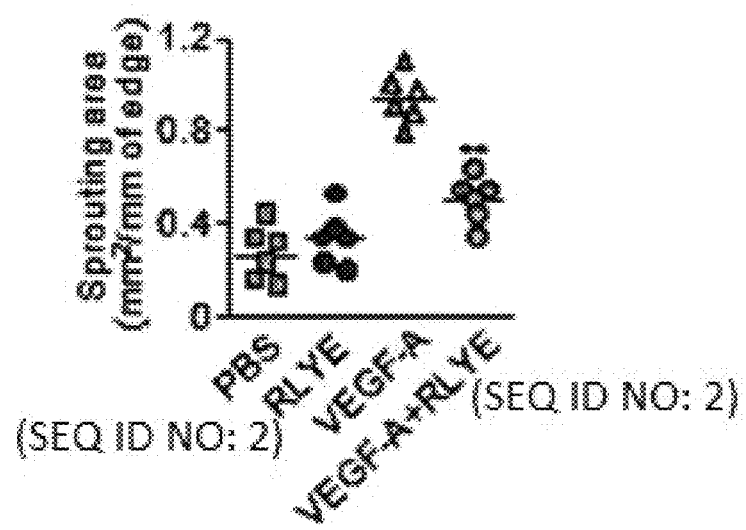
Figure 5C:
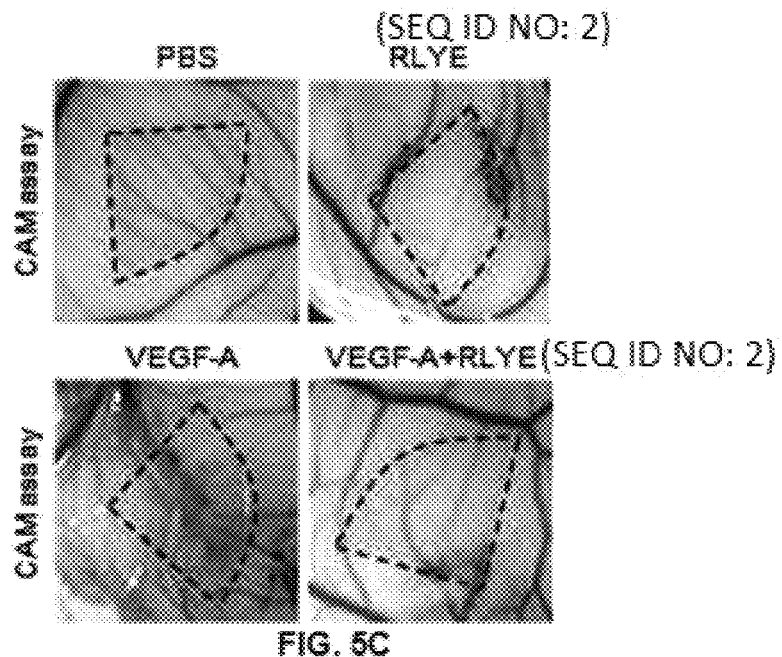
Figure 5D:
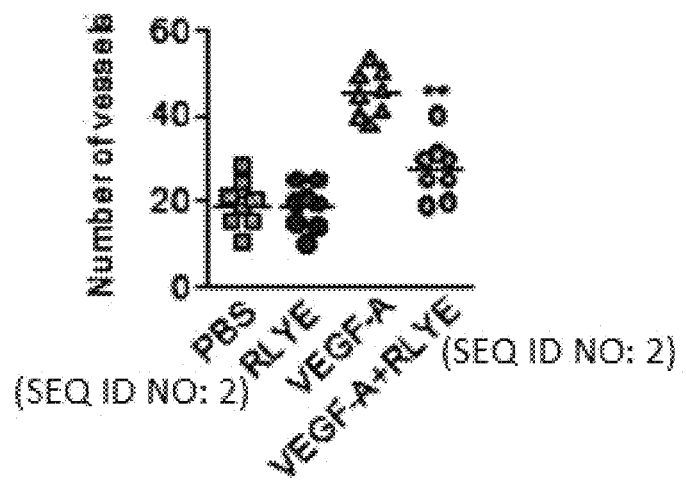
Figure 5E:
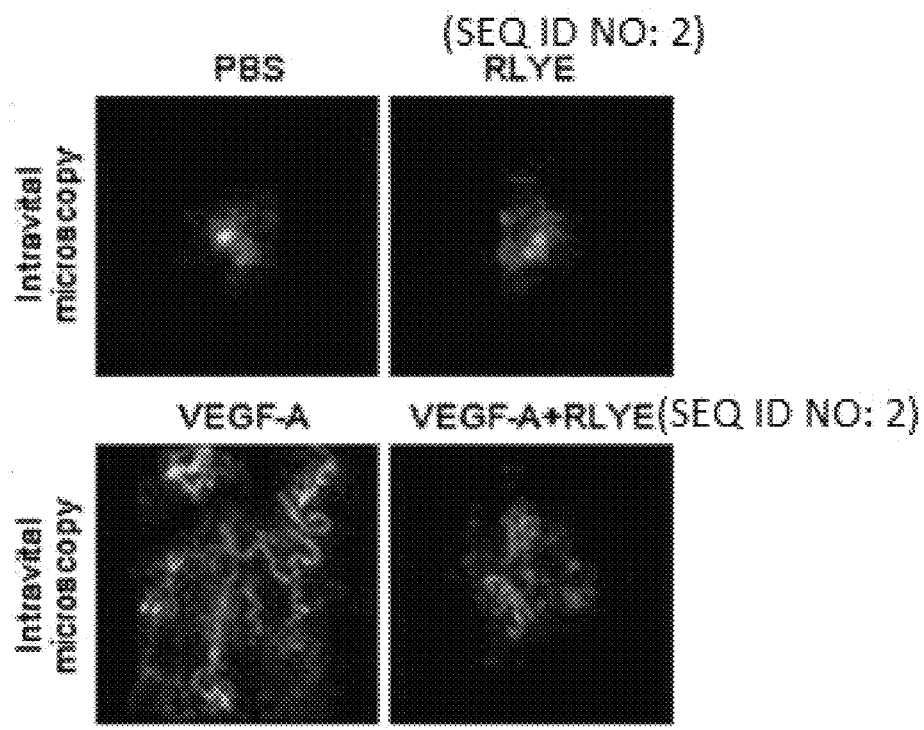
Figure 5F:
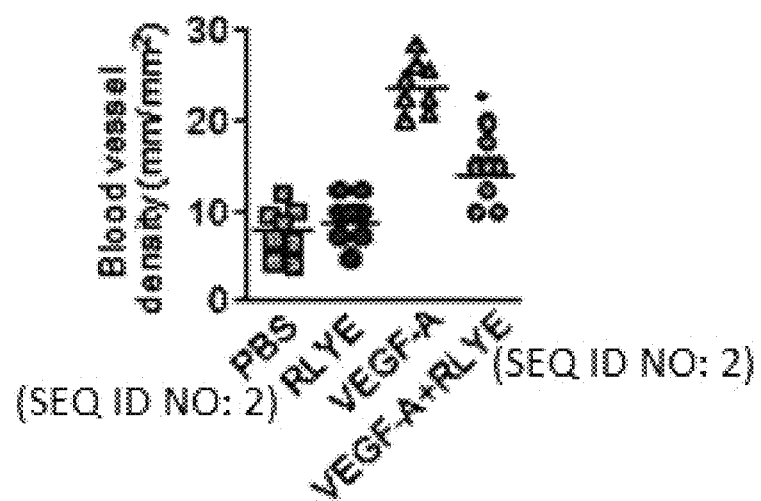

An aortic ring prepared by isolating an aorta from a mouse and slicing it into thin pieces was placed on a Matrigel-coated cell culture plate, and then coated with Matrigel thereon for fixation, thereby creating an ex vivo condition, and an effect of RLYE (SEQ ID NO: 2) on angiogenesis was investigated. When the aortic ring-fixed cell culture plate was treated with VEGF-A, angiogenesis was significantly increased at the edge of the aortic ring, and such an increase was significantly inhibited by RLYE (SEQ ID NO: 2) treatment (see FIGS. 5A and 5B). Also, as seen from CAM analysis using fertilized eggs to investigate the angiogenesis regulatory effect of RLYE (SEQ ID NO: 2), the RLYE (SEQ ID NO: 2) treatment caused a considerable reduction in the increased blood vessel density due to VEGF-A-induced production of capillaries (see FIGS. 5C and 5D). Moreover, as a result of biomicroscopy for confirming the anti-angiogenic function of RLYE (SEQ ID NO: 2) in a mouse model, the RLYE (SEQ ID NO: 2) administration effectively inhibited VEGF-A-induced angiogenesis (production of capillaries, formation of new blood vessels, etc.) (see FIGS. 5E and 5F). Such a result demonstrates that RLYE (SEQ ID NO: 2) is able to inhibit VEGF-A-induced formation of new blood vessels in vivo.

Figure 6A:
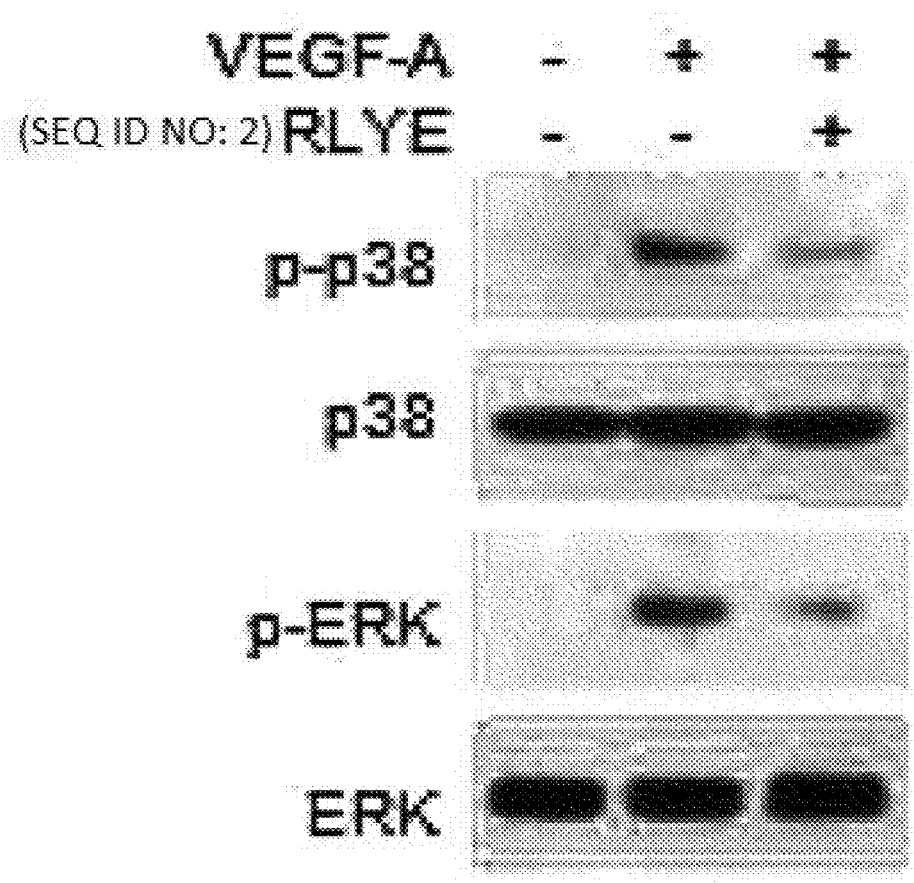
FIGS. 6A, 6B, 6C, 6D and 6E show western blots demonstrating the effect of an RLYE (SEQ ID NO: 2) peptide on VEGF-A-induced angiogenesis signaling (FIG. 6A: inhibitory effect on p38MAPK and ERK phosphorylation, FIG. 6B: inhibitory effect on Src and FAK phosphorylation, FIG. 6C: inhibitory effect on Akt phosphorylation, FIG. 6D: inhibitory effect on eNOS phosphorylation, FIG. 6E: inhibitory effect on VEGFR-2 phosphorylation, graph value: mean±standard deviation (n=3), for VEGF-A only-treated group, **P<0.01)
Figure 6B:
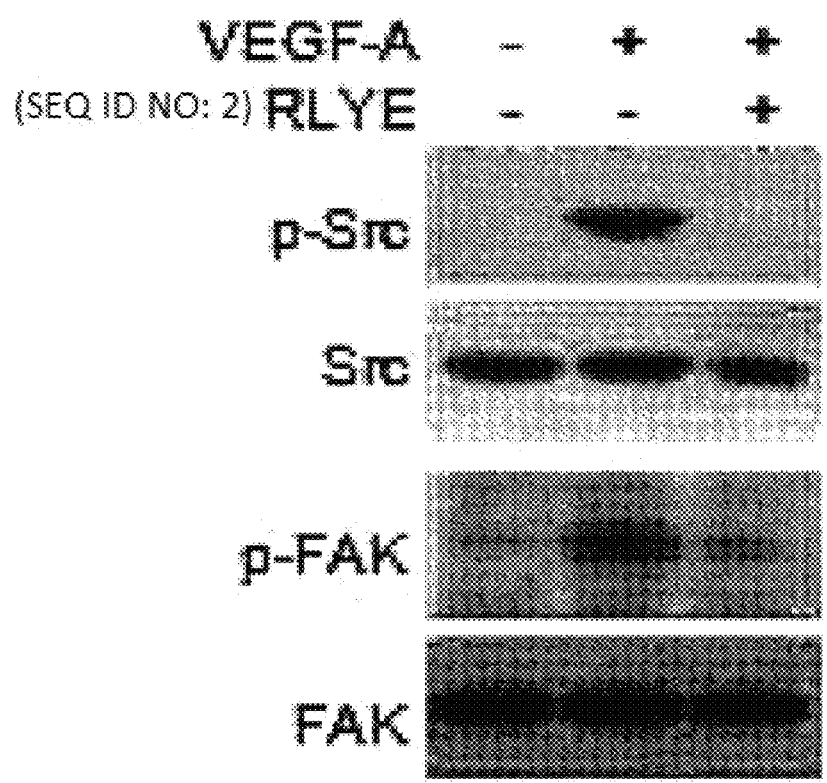
Figure 6C:
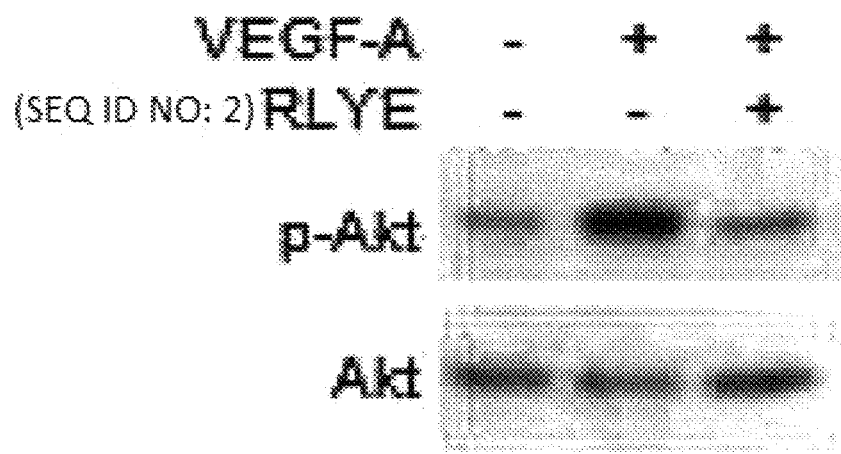
Figure 6D:
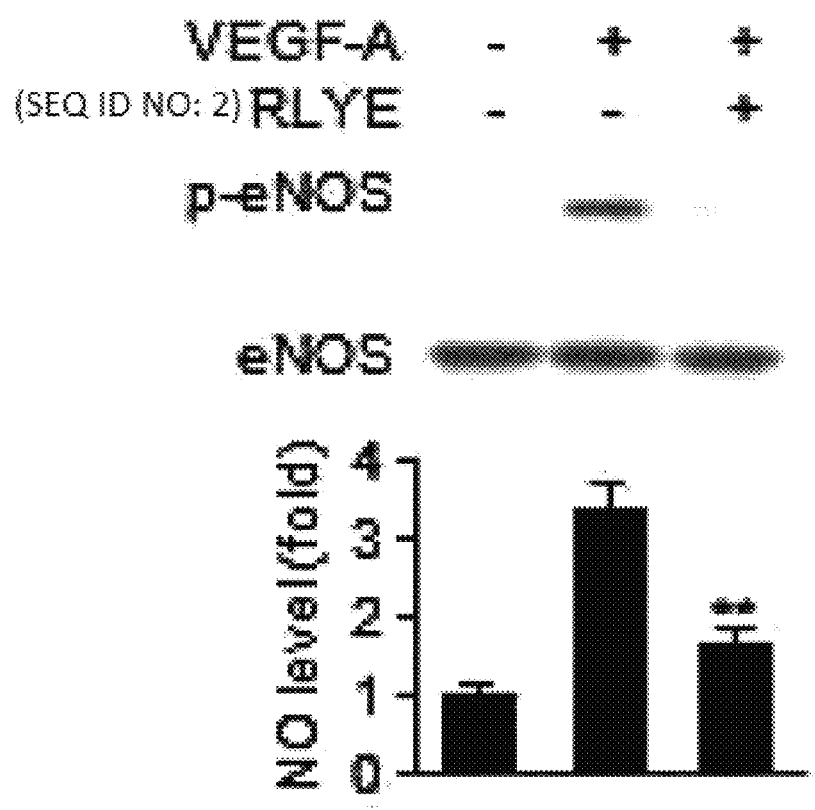
Figure 6E:
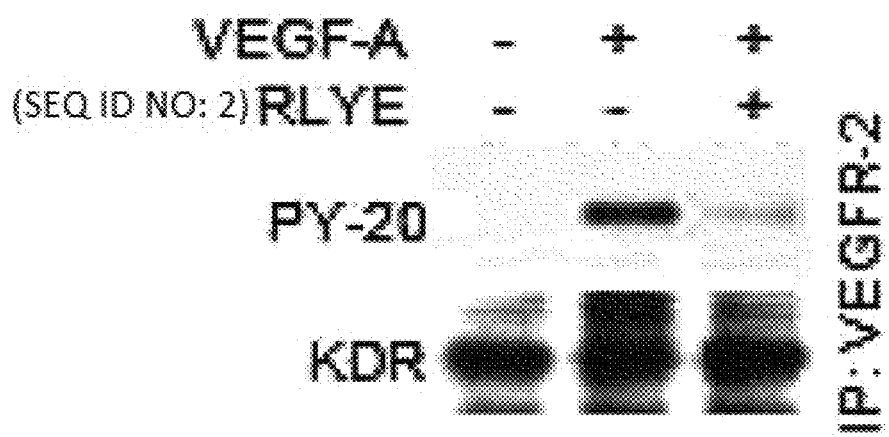

2-6. Effect of Disturbing VEGF-Induced Angiogenesis Signaling Through Inhibition of VEGFR-2 Activity VEGF activates various types of cell signaling through activation of a VEGF receptor-2, resulting in induction of angiogenesis. Therefore, to investigate a molecular mechanism in which RLYE (SEQ ID NO: 2) inhibits VEGF-induced angiogenesis, the effect of RLYE (SEQ ID NO: 2) on a cell signaling event initiated by VEGF-A was examined. As HUVECs stimulated with VEGF-A were treated with RLYE (SEQ ID NO: 2), activation of signaling mediators p38 and ERK for cell proliferation, which is the main pathway of angiogenesis signaling, phosphorylation of signaling mediators Src and FAK for cell migration, and phosphorylation of signaling mediator Akt for cell survival were inhibited (see FIG. 6A to 6C). Also, it was seen that RLYE (SEQ ID NO: 2) effectively blocked VEGF-A-induced phosphorylation of an NO synthase (eNOS) and NO production of the HUVECs (see FIG. 6D), and it is known that the inhibition of eNOS/NO pathways inhibits angiogenesis and the blood vessel function. Furthermore, it was seen that RLYE (SEQ ID NO: 2) inhibits the phosphorylation of VEGFR-2, which is the most significant angiogenesis signal, in the VEGF-A-treated HUVECs (see FIG. 6E). Such results demonstrate that RLYE (SEQ ID NO: 2) inhibits VEGFR-2 phosphorylation, resulting in inhibition of a VEGF-A-induced angiogenesis signaling process.

2-7. Effect on bFGF, EGF and S1P-Induced Angiogenesis

Figure 7A:
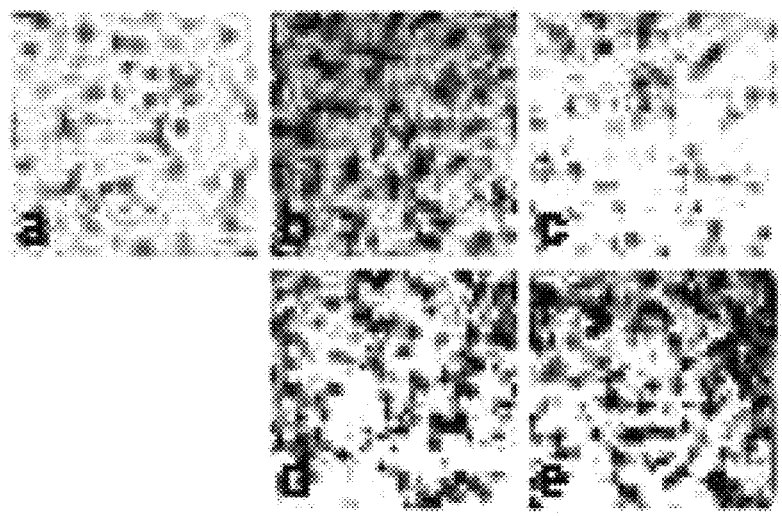
FIGS. 7A, 7B, 7C, 7D, 7E, and 7F show the effects of an RLYE (SEQ ID NO: 2) peptide on in vitro angiogenesis induced by VEGF-A, a base fibroblast growth factor (bFGF), an epithelial cell growth factor (EGF), and sphingosine-1-phosphate (S1P) (FIG. 7A, FIG. 7B, FIG. 7E and FIG. 7F: inhibitory effects on vascular endothelial cell migration using Boyden chamber assay, FIG. 7C and FIG. 7D: inhibitory effects on tube formation in vascular endothelial cells, graph value: mean±standard deviation (n=3), for VEGF-A only-treated group, *P<0.05,**P<0.01)
Figure 7B:
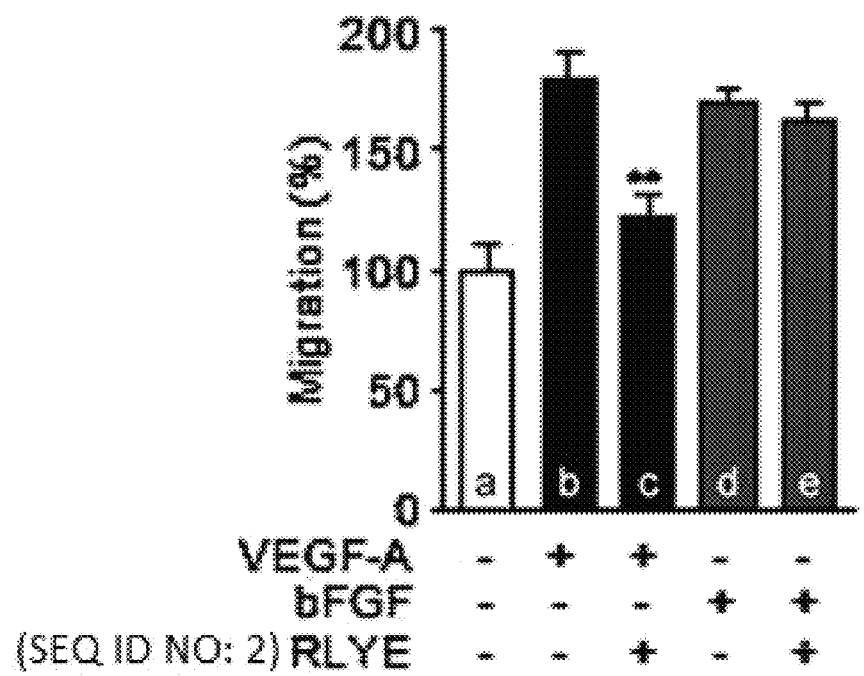
Figure 7C:
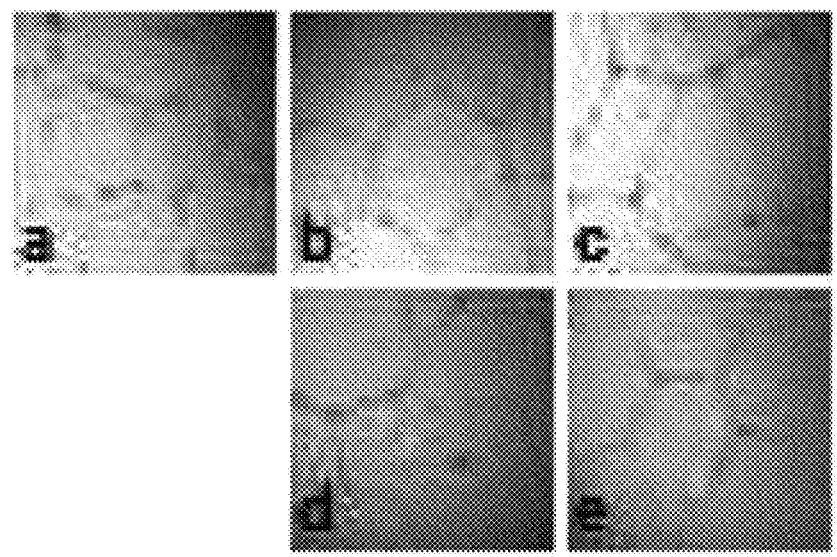
Figure 7D:
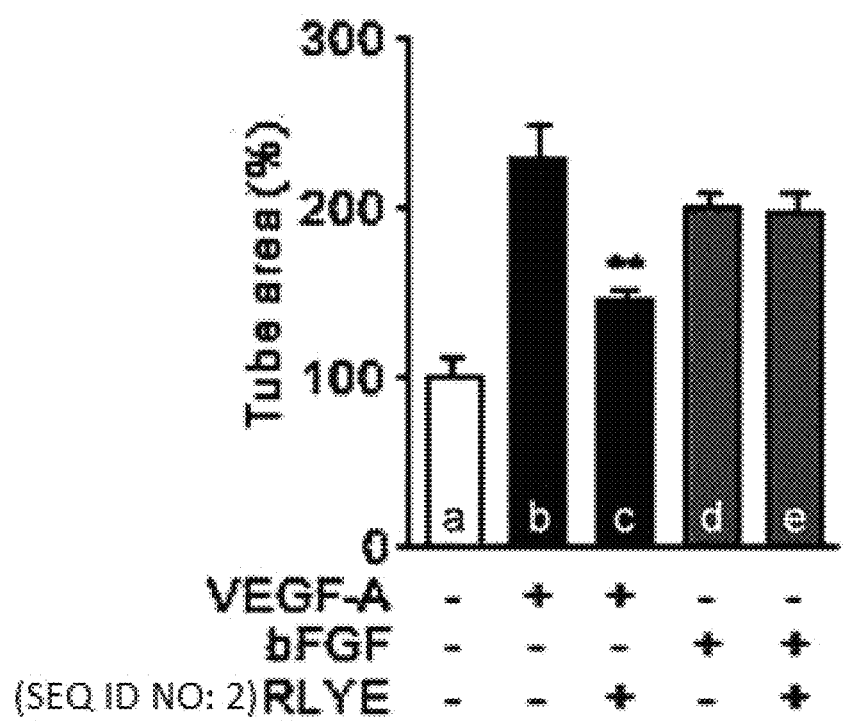
Figure 7E:
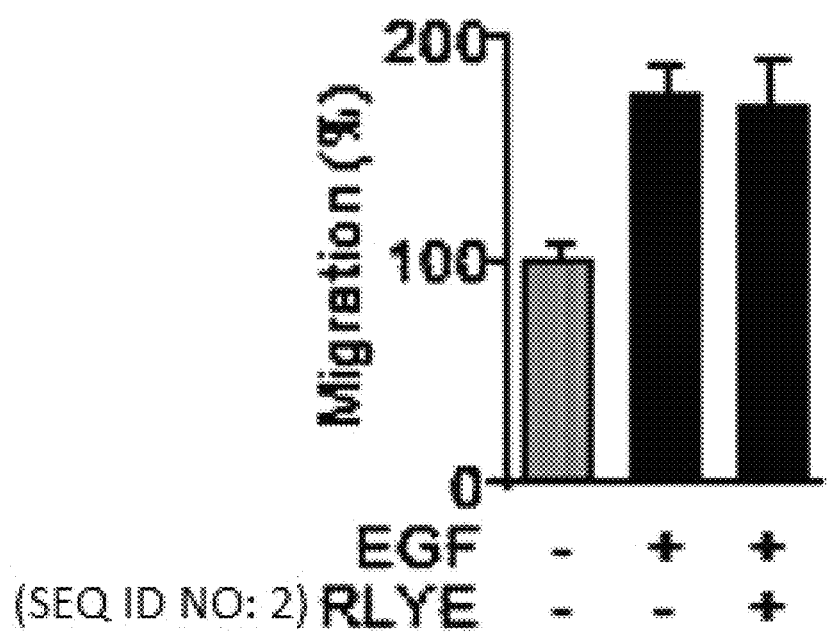
Figure 7F:
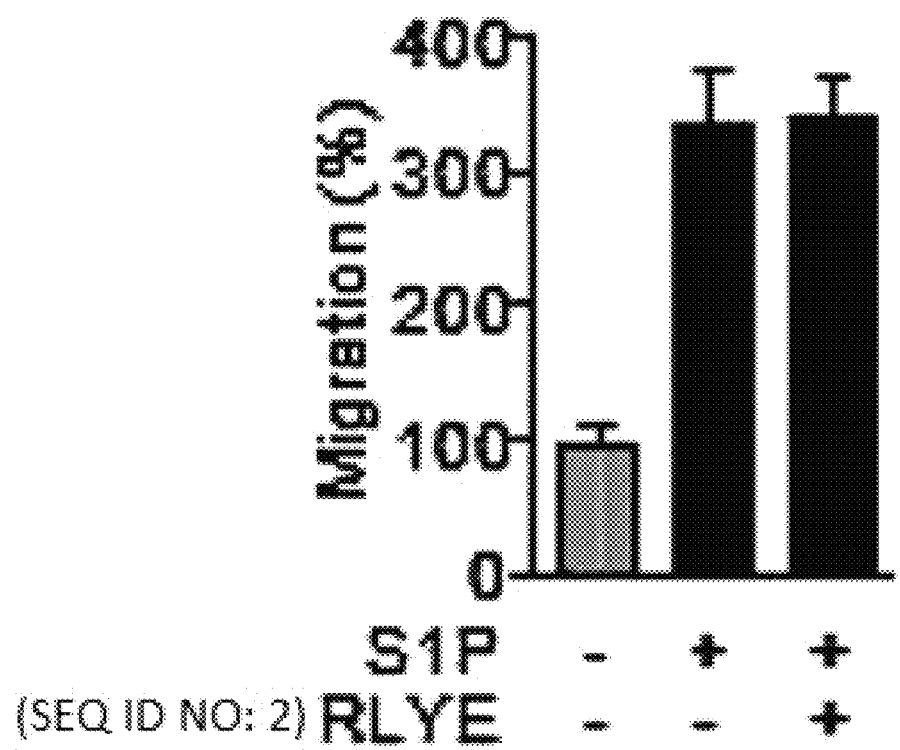

It was investigated whether RLYE (SEQ ID NO: 2) is also able to regulate angiogenesis induced by other angiogenic factors such as bFGF, EGF and S1P. Under HUVEC culture conditions, RLYE (SEQ ID NO: 2) did not inhibit bFGF-induced migration and tube formation of HUVECs, but effectively inhibited VEGF-A-mediated angiogenesis (see FIGS. 7A, 7B, 7C, and 7D). Also, it was seen that RLYE (SEQ ID NO: 2) does not affect EGF-induced migration of HUVECs, either (see FIG. 7E). The HUVEC migration induced by S1P, which is a biologically active lipid for stimulating angiogenesis, was not inhibited by RLYE (SEQ ID NO: 2), either (see FIG. 7F). Such results demonstrate that RLYE (SEQ ID NO: 2) inhibits VEGF-A-induced angiogenesis, but does not inhibit angiogenesis induced by other angiogenesis factors including bFGF, EGF and S1P.

2-8. Effect on VEGFR-2 or VEGFR-1-Mediated Angiogenesis

Figure 8A:
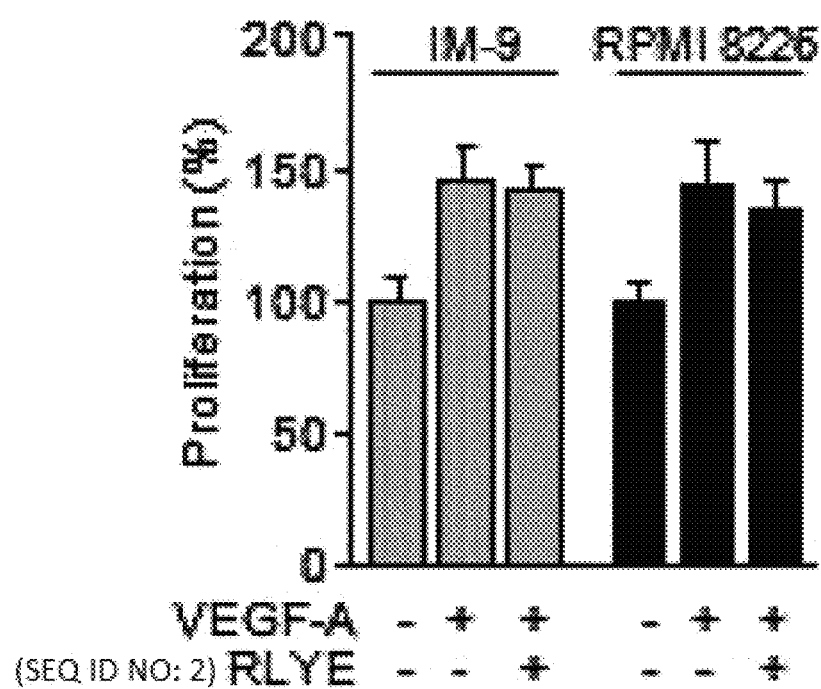
FIGS. 8A, 8B, 8C and 8D show the effect of an RLYE (SEQ ID NO: 2) peptide on in vitro angiogenesis induced by VEGFR-2 and VEGFR-1 (FIG. 8A: inhibitory effect on vascular endothelial cell growth ([3H]-thymidine incorporation assay), FIG. 8B and FIG. 8C: inhibitory effect on vascular endothelial cell migration using Boyden chamber assay, FIG. 8D: inhibitory effect on ERK phosphorylation, graph value: mean±standard deviation(n=3), for VEGF-A only-treated group, **P<0.01)
Figure 8B:
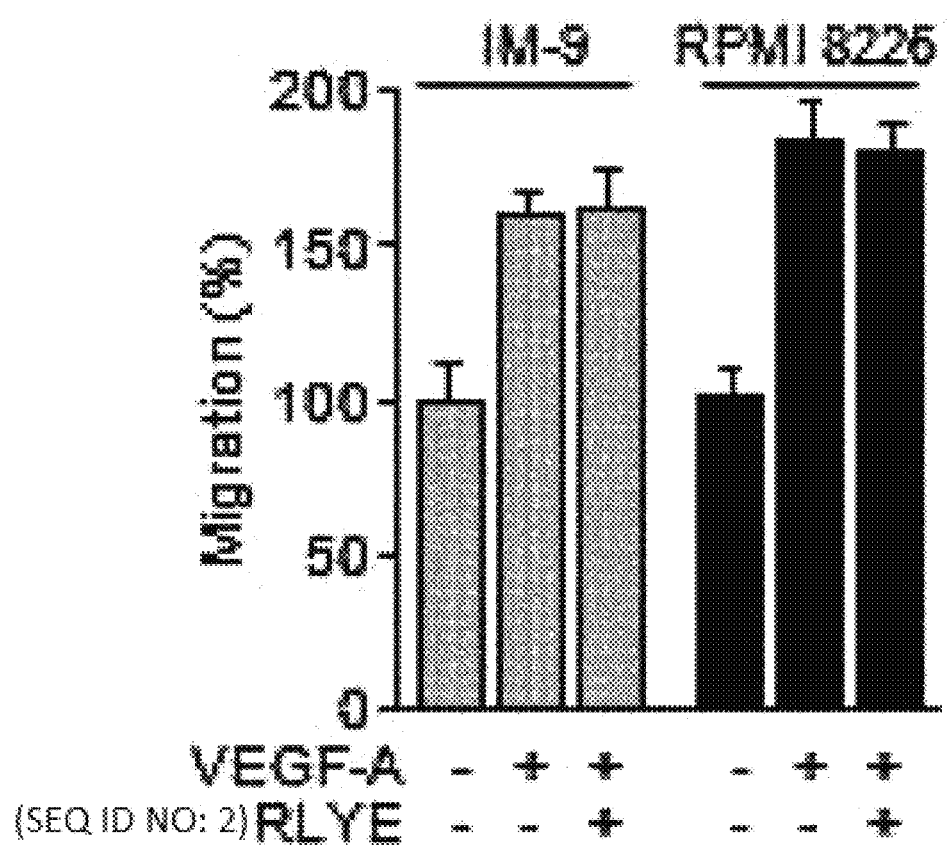
Figure 8C:
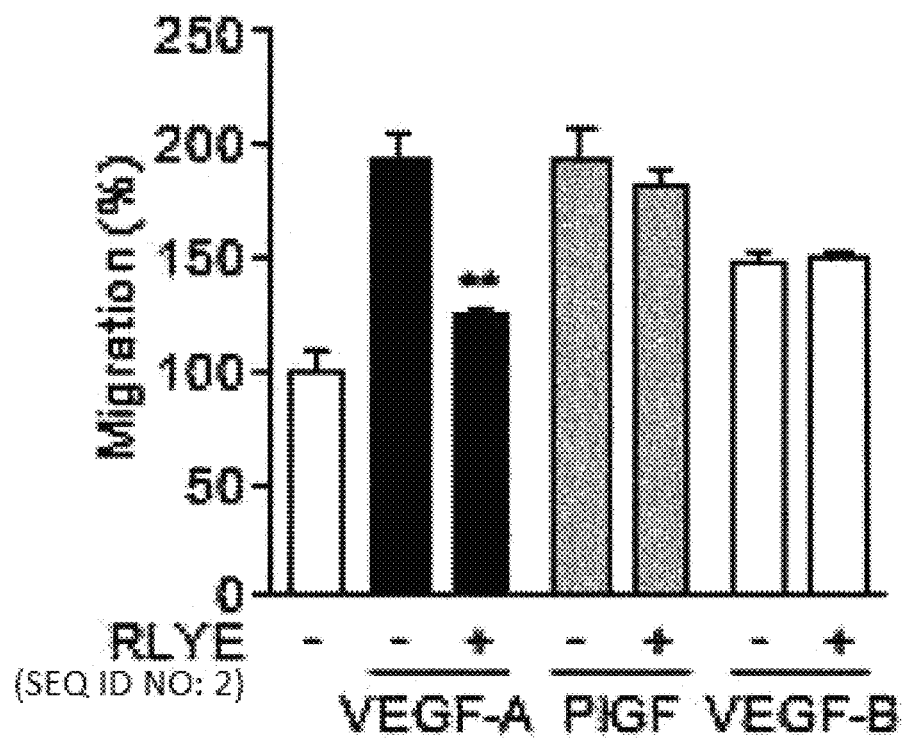
Figure 8D:
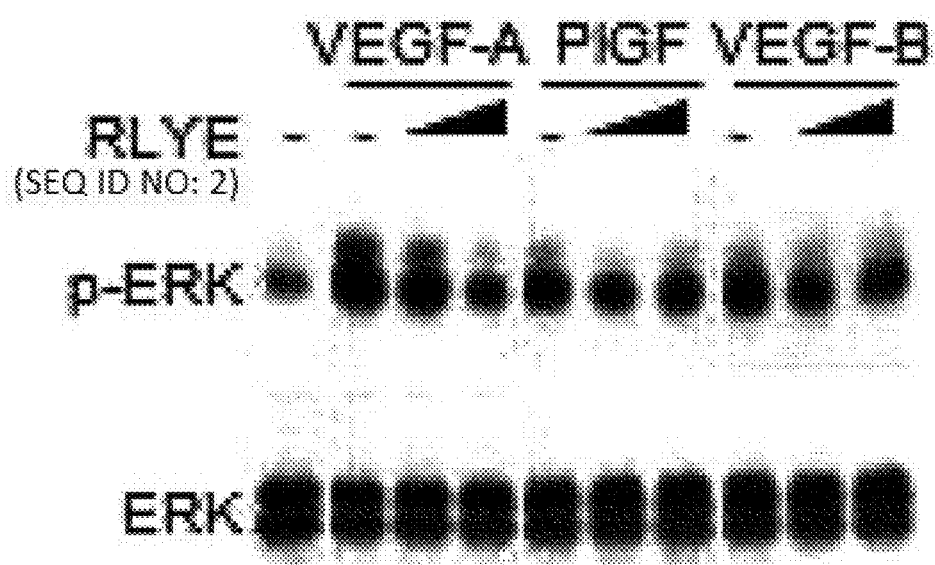

VEGF-A activates both VEGFR-1 and VEGFR-2, expressed in HUVECs. Therefore, it was investigated whether RLYE (SEQ ID NO: 2) inhibits either or all of the above receptors. Two types of multiple myeloma (MM) cells (IM-9 and RPMI 8226 cells) expressed VEGFR-1, but did not express VEGFR-2. By using these cells, the function of RLYE (SEQ ID NO: 2) affecting the activity of VEGFR-1 may be identified. When these cells were treated with RLYE (SEQ ID NO: 2), cell proliferation and migration induced by VEGF-A were not inhibited (see FIGS. 8A and 8B). In a more elaborate experiment, the effect of RLYE (SEQ ID NO: 2) on HUVECs stimulated with VEGF-A (ligand of VEGFR-1/2), P1GF (ligand of VEGFR-1) and VEGF-B (ligand of VEGFR-1) was verified. According to the experiment, it was seen that RLYE (SEQ ID NO: 2) certainly inhibits the VEGF-A-induced HUVEC migration, but does not inhibit P1GF and VEGF-B-induced cell migration (see FIG. 8C). As expected, RLYE (SEQ ID NO: 2) inhibited VEGF-A-induced ERK phosphorylation, but did not inhibit P1GF and VEGF-B-induced ERK phosphorylation (see FIG. 8D). Such results demonstrate that RLYE (SEQ ID NO: 2) inhibits VEGFR-2-induced angiogenesis, but does not inhibit VEGFR-1-induced angiogenesis.

2-9. Interaction with VEGFR-2 or VEGFR-1

Figure 9A:
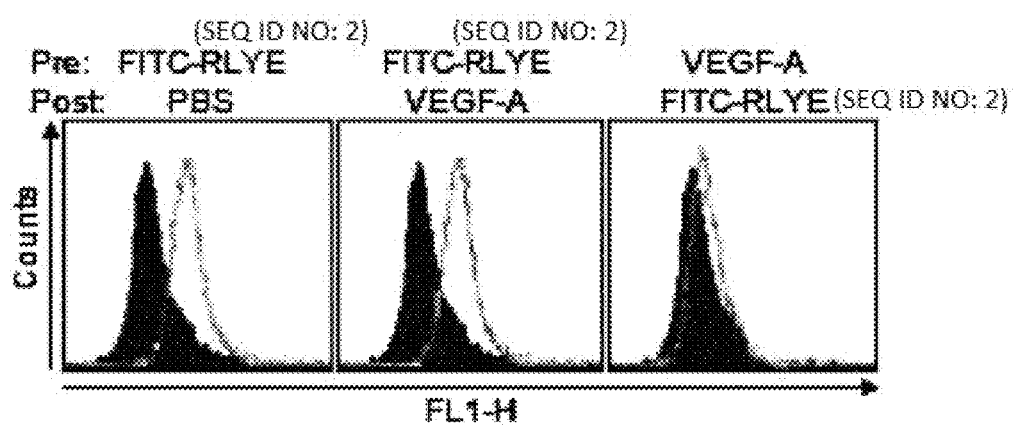
FIGS. 9A, 9B, 9C and 9D show the interaction between an RLYE (SEQ ID NO: 2) peptide and VEGFR-2 (FIG. 9A: FACS results for vascular endothelial cells using FITC-binding RLYE (SEQ ID NO: 2), FIG. 9B: vascular endothelial cells to which FITC-binding RLYE (SEQ ID NO: 2) peptide and TRITC-binding PECAM-1 antibody are linked, observed under a confocal microscope, FIG. 9C and FIG. 9D: binding of biotinylated RLYE (SEQ ID NO: 2) peptide to VEGFR-1 or VEGFR-2, confirmed by pull-down analysis)
Figure 9B:
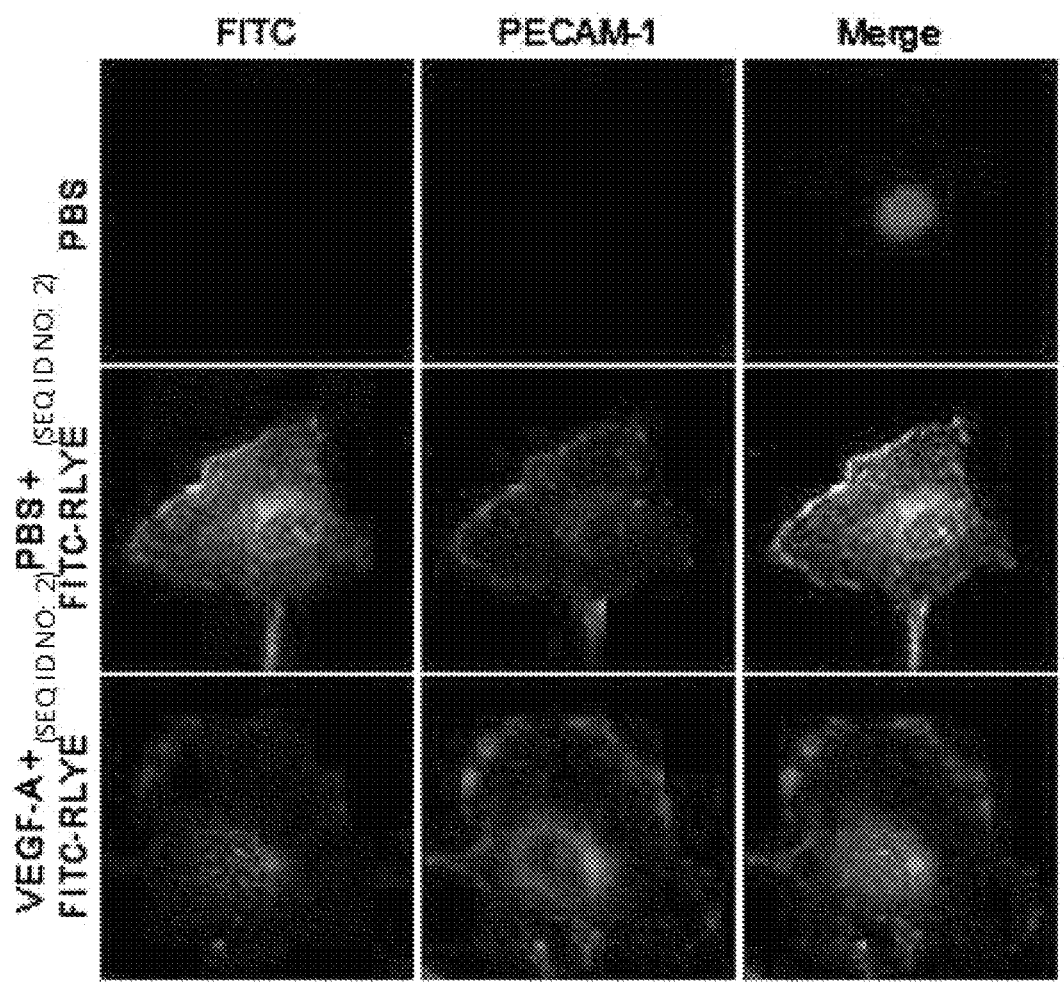
Figure 9C:
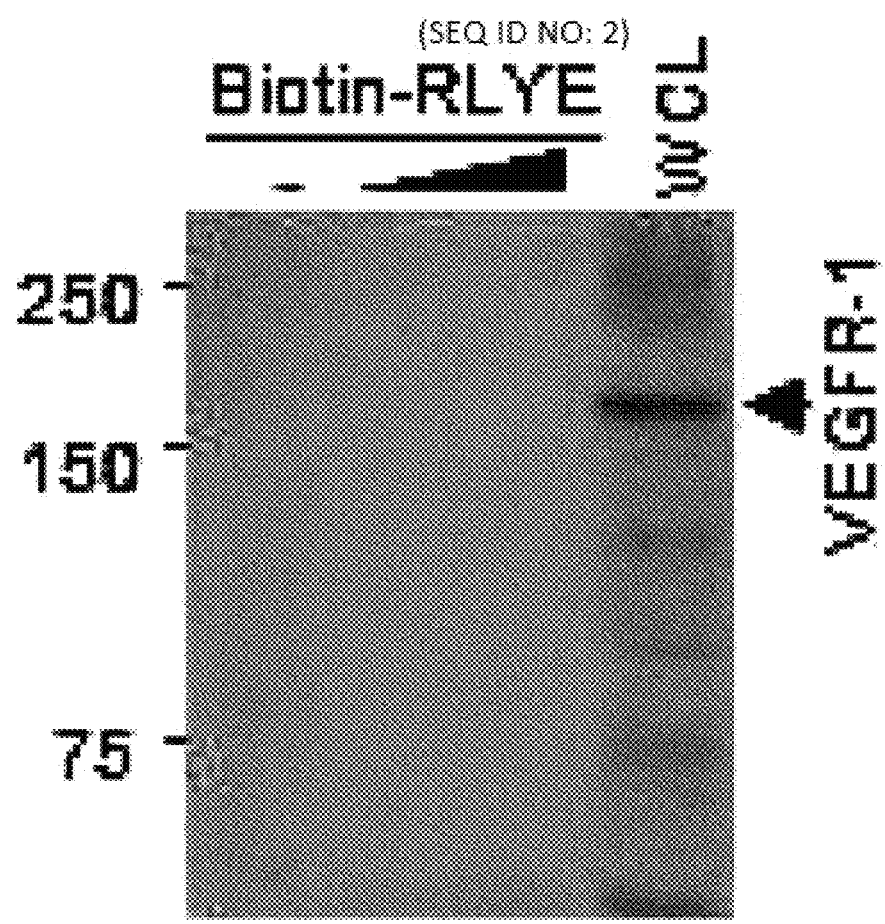
Figure 9D:
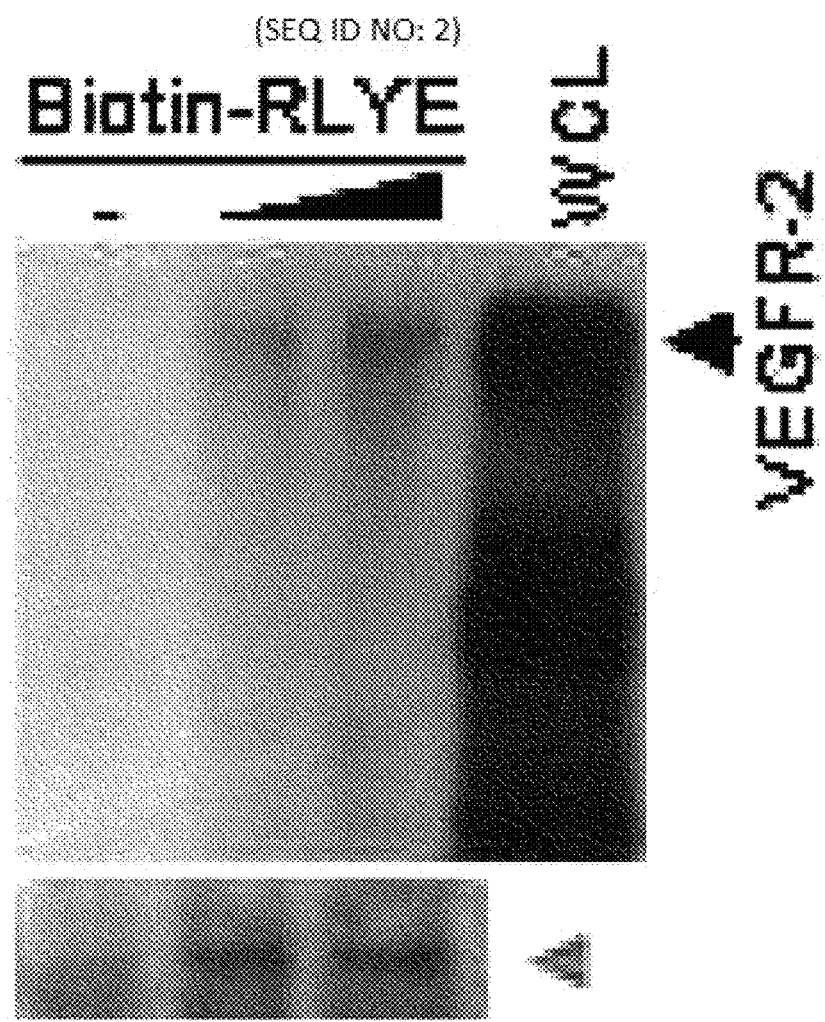
Figure 10A:
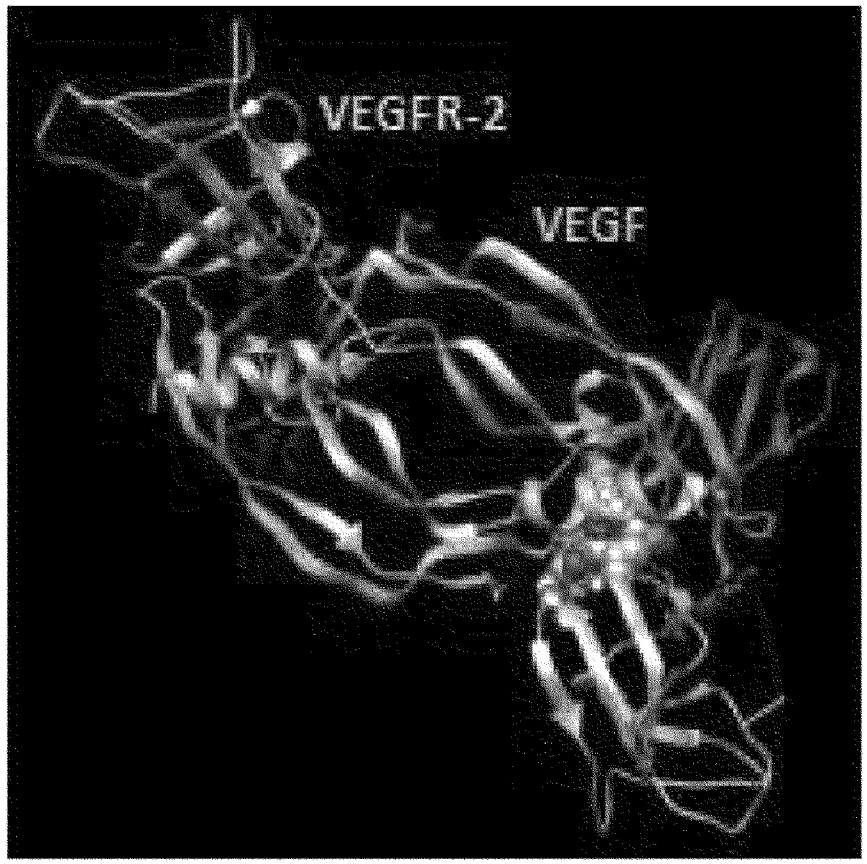
FIGS. 10A, 10B, 10C and 10D show the interaction between an RLYE (SEQ ID NO: 2) peptide and VEGFR-2 (FIG. 10A: binding conformation of RLYE (SEQ ID NO: 2) affecting interaction between VEGFR-2 and VEGF, FIG. 10B: binding between RLYE (SEQ ID NO: 2) and VEGFR-2 according to properties of amino acids, FIG. 10C: interaction between amino acids of RLYE (SEQ ID NO: 2) and VEGFR-2, FIG. 10D: SPR result describing binding between RLYE (SEQ ID NO: 2) and VEGFR-2)
Figure 10B:
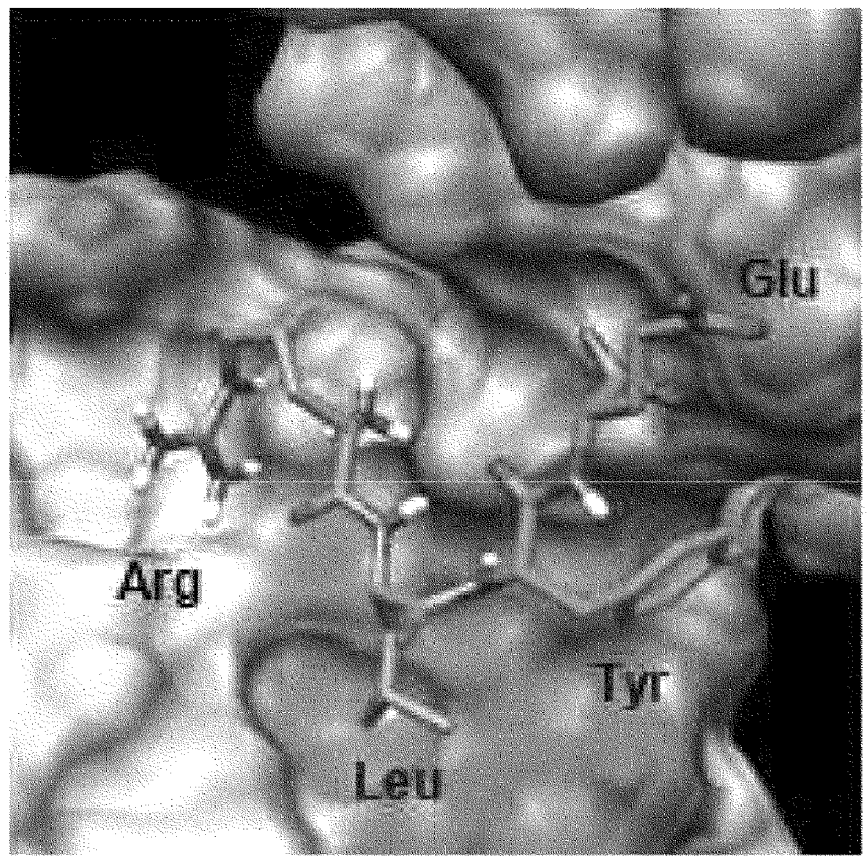
Figure 10C:
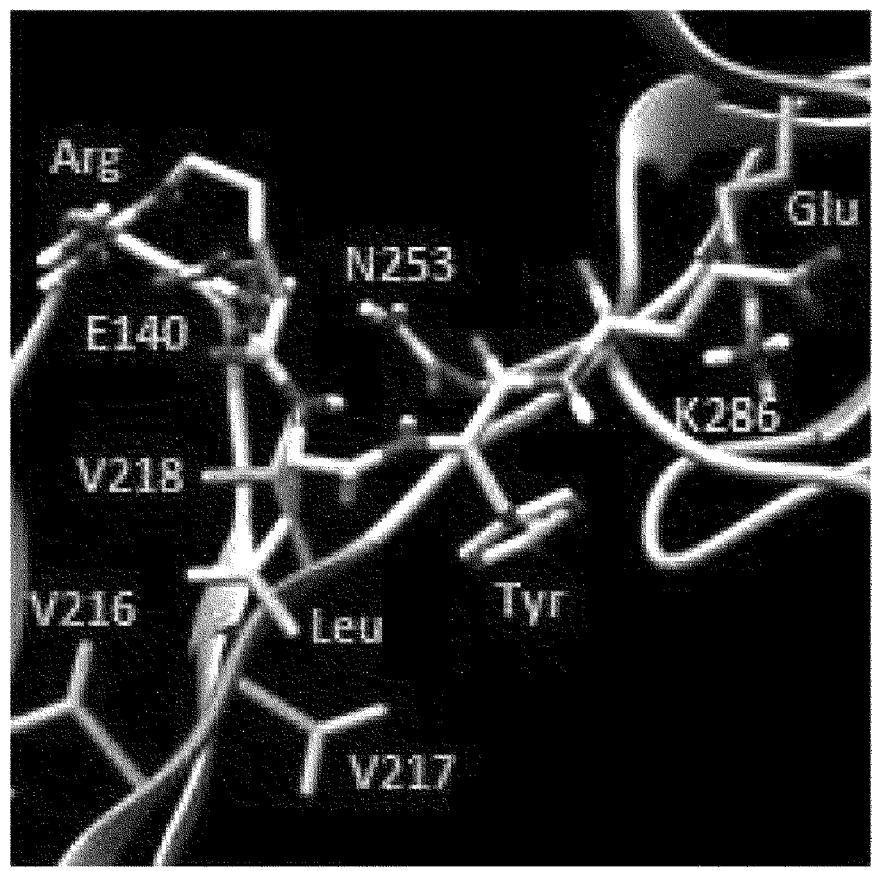

Subsequently, it was investigated whether RLYE (SEQ ID NO: 2) interacts with VEGFR-2 expressed in HUVECs. HUVECs were cultured with FITC-RLYE (SEQ ID NO: 2) before or after VEGF-A treatment, and FACS was performed to examine an amount of RLYE (SEQ ID NO: 2) binding to the HUVECs. As a result of the FACS, FITC-RLYE (SEQ ID NO: 2) bound to a cell surface which was not treated with VEGF-A, but did not bind to a VEGF-A-pretreated cell (see FIG. 9A). As examined using a confocal microscope under similar experimental conditions to those described above, it was seen that RLYE (SEQ ID NO: 2) binds to a HUVEC surface, such binding was effectively blocked by the pretreatment of VEGF-A, and the binding of RLYE (SEQ ID NO: 2), along with PECAM-1, which is a HUVEC marker, takes place only on the surface of the cell membrane of HUVEC (see FIG. 9B). To examine binding between RLYE (SEQ ID NO: 2) and VEGF receptors, a pull-down assay was performed. As a result, it was seen that RLYE (SEQ ID NO: 2) binds to VEGFR-2, but does not bind to VEGFR-1 (see FIGS. 9C and 9D). In addition, to prove the interaction between RLYE (SEQ ID NO: 2) and VEGFR-2, docking analysis was performed. Therefore, the binding between RLYE (SEQ ID NO: 2) and VEGFR-2 was identified as a strong bond having a small dissociation coefficient (194 nM), and it was also seen that RLYE (SEQ ID NO: 2) binds to VEGFR-2 at the same positions to which VEGF-A/C binds (immunoglobulin homology domains D2 and D3) (see FIG. 10A). Interestingly, it was seen that charged residues placed at the both ends of the peptide interact with hydrophilic pockets of VEGF, and the remaining uncharged residues are placed at hydrophobic domains (see FIG. 10B). It was confirmed that Arg and Glu residues placed at the ends of the peptide electrostatically interact with Glu140 and Lys286 of VEGFR-2, respectively, and Lys286 forms a salt bridge with Glu64 of VEGF-A (see FIG. 10C). Also, the Arg residue also forms a hydrogen bond with Asn253, which is the key amino acid of VEGFR-2 binding to VEGF-A. Leu is in contact with a hydrophobic domain of Val216-218 of VEGFR-2 to stimulate a hydrophobic interaction between RLYE (SEQ ID NO: 2) and VEGFR-2. The Val216-218 residue of VEGFR-2 is known to form a hydrophobic interaction with VEGF-A. Meanwhile, in Tyr, an aromatic ring structure also forms a hydrophobic interaction with the Val216-218 residue of VEGFR-2, and a hydroxide group forms a hydrogen bond with the amide-carbonyl of Asn253. Such results demonstrate that RLYE (SEQ ID NO: 2) binds to VEGF-A at the same position to which VEGFR-2 binds, and thus disturbs binding of VEGF-A to VEGFR-2.

Figure 10D:
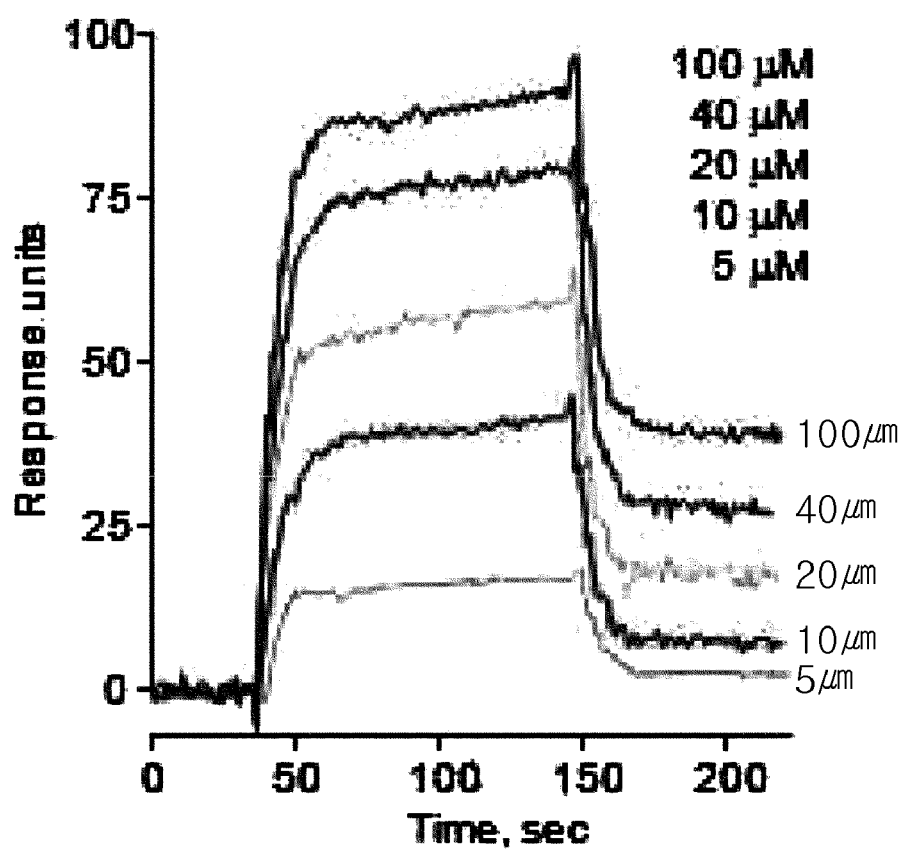

Meanwhile, the interaction between RLYE (SEQ ID NO: 2) and rhVEGFR-2 was examined by SPR analysis. As a result, it was confirmed that RLYE (SEQ ID NO: 2) effectively binds to rhVEGFR-2, and the Kd of RLYE (SEQ ID NO: 2) binding to VEGFR-2 was calculated to be 9.0 μM (see FIG. 10D). Such a result demonstrates that the binding between VEGF-A and VEGFR-2 is disturbed by the interaction between RLYE (SEQ ID NO: 2) and VEGFR-2, resulting in inhibiting the angiogenic activity of VEGF-A.

2-10. Effect of Inhibiting Growth and Metastasis of Melanoma in Mouse Model

Figure 11A:
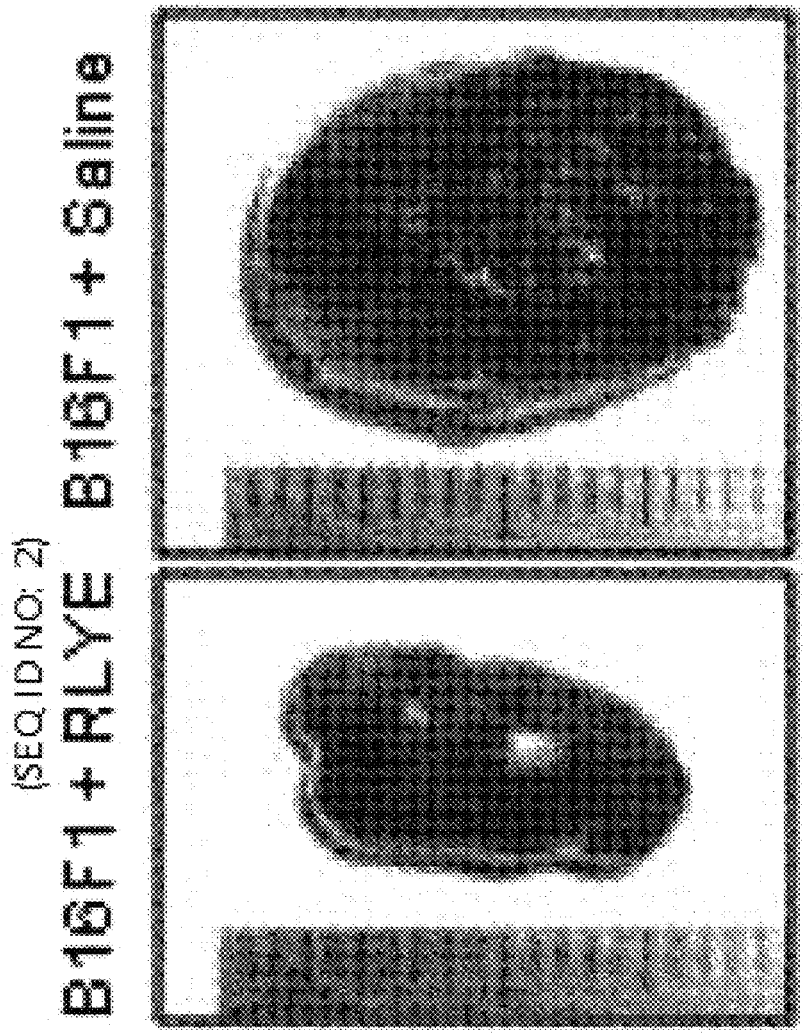
FIGS. 11A, 11B, 11C, 11D, 11E, 11F, 11G, 11H and 11I show the effect of an RLYE (SEQ ID NO: 2) peptide on tumor growth and metastasis in a mouse model (FIG. 11A: size of melanoma (B16F1) according to RLYE (SEQ ID NO: 2) treatment, FIG. 11B: weight of melanoma (B16F1) according to RLYE (SEQ ID NO: 2) treatment, FIG. 11C: inhibition of melanoma (B16F1) growth over RLYE (SEQ ID NO: 2) treating time, FIG. 11D: inhibition of metastasis of melanoma cells to lung according to RLYE (SEQ ID NO: 2) treatment, FIG. 11E: quantitative analysis result for metastasis of melanoma cells (B16F10), FIG. 11F: size of human colorectal tumor (HCT116) according to RLYE (SEQ ID NO: 2) treatment, FIG. 11G: inhibition of colorectal tumor(HCT116) growth over RLYE (SEQ ID NO: 2) treating time, FIG. 11H: analysis of hemoglobin concentration in colorectal tumor tissue, FIG. 11I: inhibition of cancer angiogenesis in colorectal tumor by RKYE (SEQ ID NO: 2) treatment through immunostaining using isolectin B4 and a PECAM-1 antibody, graph value: mean±standard deviation, for saline only-treated group, *P<0.05, **P<0.01).
Figure 11B:
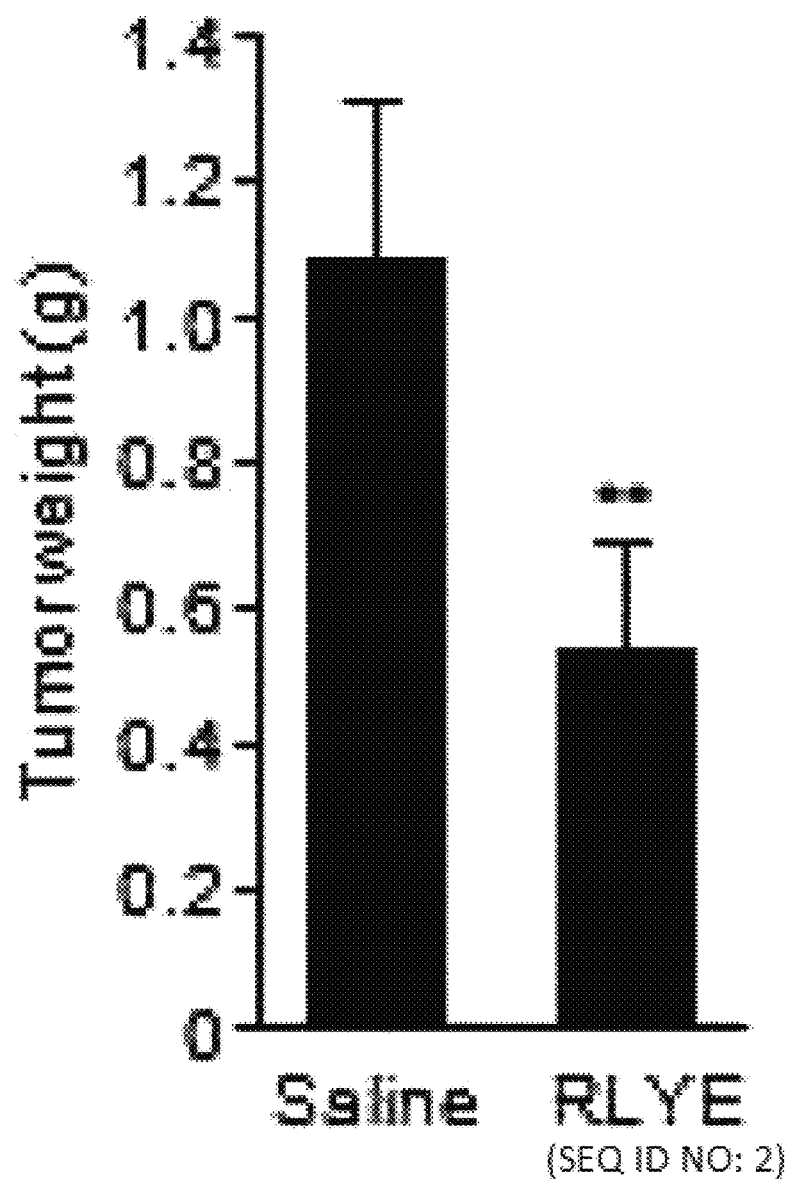
Figure 11C:
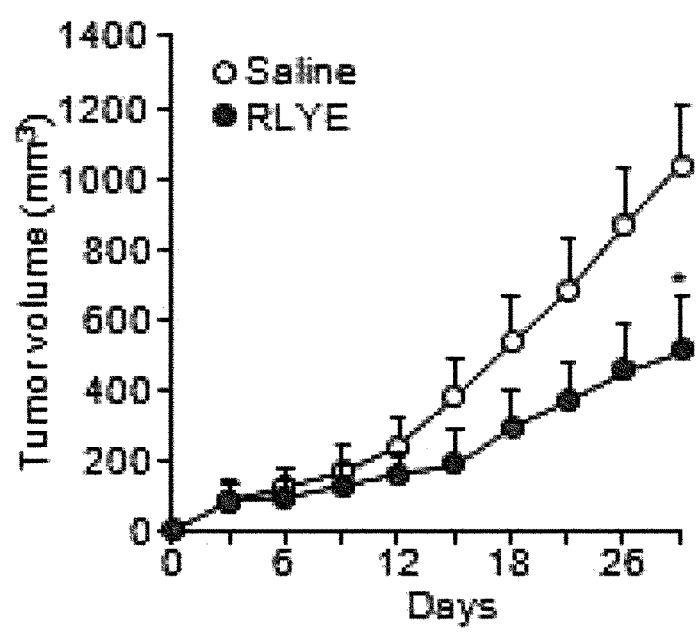
Figure 11D:
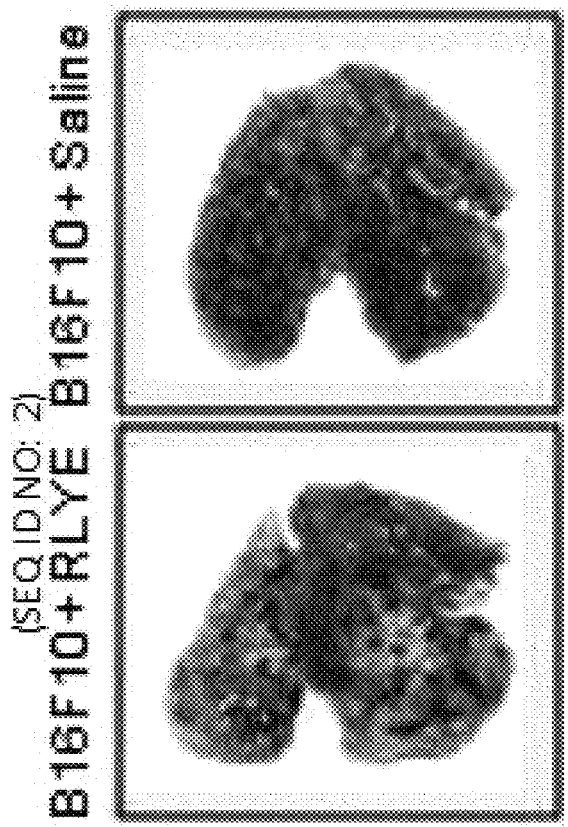
Figure 11E:
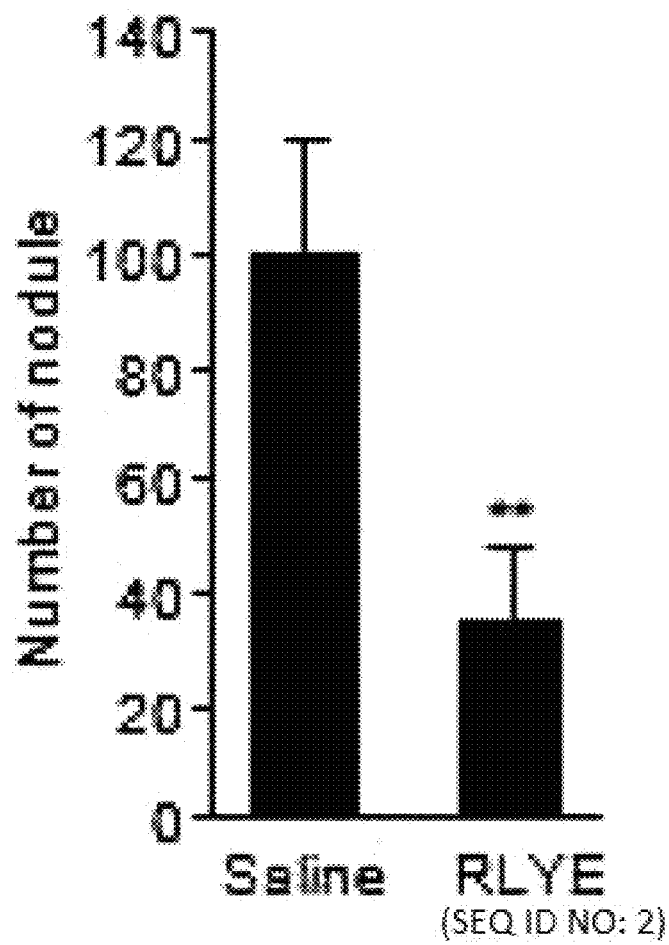

Since VEGFR-2 crucially acts on tumor angiogenesis, a pharmaceutical effect of RLYE (SEQ ID NO: 2) on tumor growth and metastasis in a mouse model was investigated. B16F1 melanoma cells were subcutaneously injected into a side of a mouse, and RLYE (SEQ ID NO: 2) was peritoneally injected with a dose of 1 mg/kg per day. Due to the RLYE (SEQ ID NO: 2) treatment, tumor size, weight and growth were significantly decreased (see FIGS. 11A to 11C). To investigate an effect of RLYE (SEQ ID NO: 2) on metastasis of tumor cells, B16F10 melanoma cells were injected into the caudal vein of a mouse, and RLYE (SEQ ID NO: 2) was peritoneally injected with a dose of 1 mg/kg per day. After three weeks, according to the analysis of colonies spreading to the lung, it was seen that, by the RLYE (SEQ ID NO: 2) administration, the number of colonies of the tumor cells spreading to the lung was decreased by 62%, compared with an untreated control mouse (see FIGS. 11D to 11E). Such a result demonstrates that RLYE (SEQ ID NO: 2) is able to effectively inhibit tumor growth and metastasis.

Figure 11F:
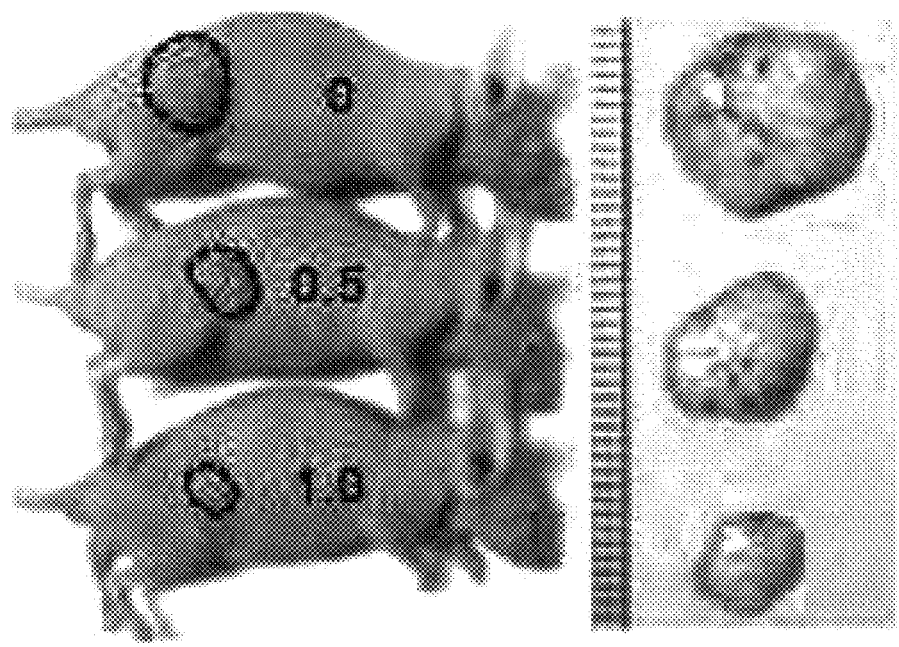
Figure 11G:
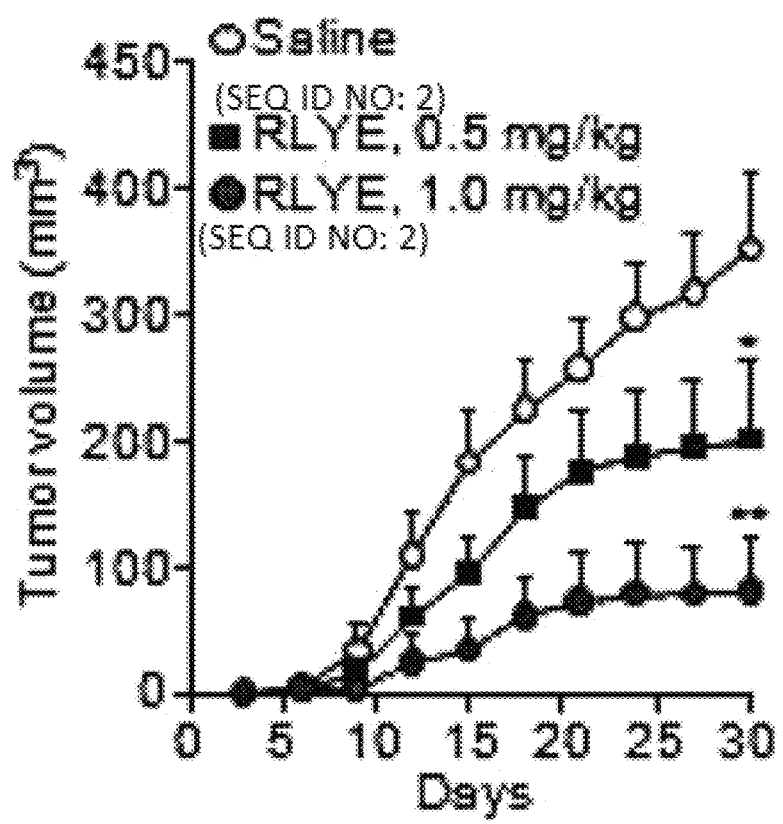
Figure 11H:
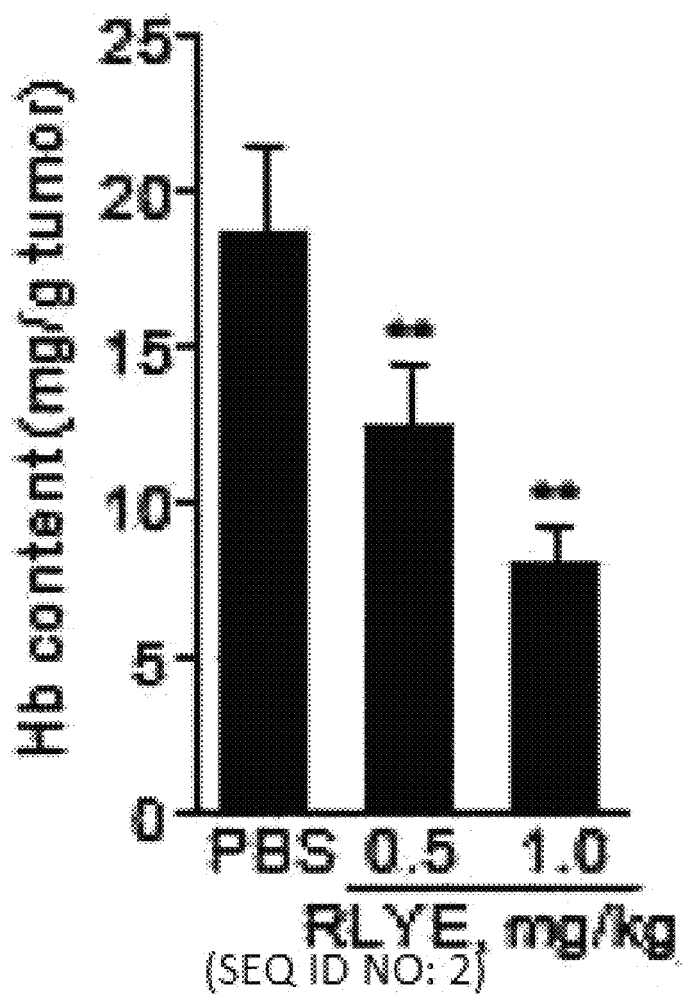
Figure 11I:
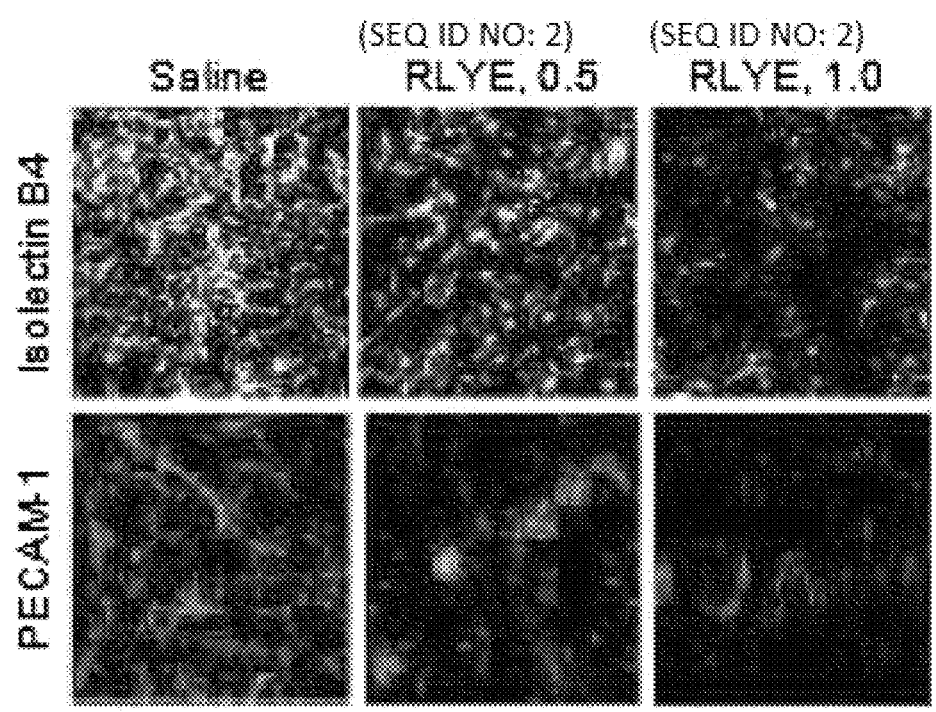

2-11. Effect of Inhibiting Growth of Human-Derived Tumor by Anti-Angiogenic Action in Mouse Model To investigate the effect of RLYE (SEQ ID NO: 2) on human tumor growth and angiogenesis in a xenograft mouse model, human colorectal tumor cells (HCT116) were subcutaneously injected into a nude mouse to generate a tumor, and then RLYE (SEQ ID NO: 2) was peritoneally injected with a dose of 0.5 or 1.0 mg/kg per day. As a result, by the RLYE (SEQ ID NO: 2) treatment, a tumor size was significantly reduced, and tumor growth was concentration-dependently inhibited (see FIGS. 11F to 11G). To analyze the density and function of blood vessels generated in tumor tissue, hemoglobin concentration in the tumor tissue was measured, and it was seen that, by the RLYE (SEQ ID NO: 2) treatment, the hemoglobin content was decreased by 41%, compared with a control (see FIG. 11H). To identify blood vessels formed in tumor tissue, immunostaining for HUVECs using FITC isolectin B4 and a PECAM-1 antibody was performed, and thereby it was shown that, due to the RLYE (SEQ ID NO: 2) treatment, invasion of the HUVECs into tumor tissue was decreased depending on the amount of treated RLYE (SEQ ID NO: 2) (see FIG. 11I). Such a result demonstrates that an RLYE peptide (SEQ ID NO: 2) effectively inhibited tumor angiogenesis, and the anti-tumor effect of RLYE (SEQ ID NO: 2) is closely associated with an anti-angiogenic effect.

According to the present invention, VEGF-induced angiogenesis or growth of cancer cells can be effectively inhibited without a risk of side effects, and therefore an excellent anticancer effect can be expected.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A peptide for inhibiting angiogenesis, consisting of:
the amino acid sequence of R-L-Y-E (SEQ ID NO: 2) or R-V-Y-E (SEQ ID NO: 3).

2. The peptide of claim 1, which inhibits angiogenesis induced by vascular endothelial growth factor A (VEGF-A).

3. A peptide for improving or treating melanoma or colorectal cancer, consisting of:
the amino acid sequence of R-L-Y-E (SEQ ID NO: 2) or R-V-Y-E (SEQ ID NO: 3).

4. The peptide of claim 3, which inhibits angiogenesis induced by vascular endothelial growth factor A (VEGF-A).

5. A method of inhibiting angiogenesis, comprising:
administering a pharmaceutically effective amount of the peptide of claim 1 to a subject in need thereof.

6. A method of improving or treating melanoma or colorectal cancer, comprising:
administering a pharmaceutically effective amount of the peptide of claim 3 to a subject in need thereof.

* * * * *